United States Patent [19]

Wong et al.

[11] Patent Number: 5,597,702
[45] Date of Patent: Jan. 28, 1997

[54] AUTOMATED LEAD ASSAY

[75] Inventors: Martin Wong, Grayslake; David M. Finley, Spring Grove; John M. Ramp, Gurnee; Gary L. Boltinghouse, Jr., McHenry, all of Ill.; Mark R. Shaffar, Kenosha, Wis.; Stephen D. Stroupe, Libertyville, Ill.; John M. Brackett, Kenosha, Wis.

[73] Assignee: Abbott Laboratories, Abbott Park, Ill.

[21] Appl. No.: 350,241

[22] Filed: Dec. 9, 1994

Related U.S. Application Data

[63] Continuation-in-part of Ser. No. 171,121, Dec. 21, 1993, abandoned, and a continuation-in-part of Ser. No. 171,035, Dec. 21, 1993, abandoned.

[51] Int. Cl.$^6$ .............................. C12Q 1/34; G01N 33/00
[52] U.S. Cl. .................. 435/18; 435/4; 435/268; 435/810; 435/962; 435/963; 436/63; 436/73; 436/74; 436/76; 514/836
[58] Field of Search .................... 435/18, 4, 268, 435/810, 962, 963; 436/63, 73, 74, 76; 514/836

[56] References Cited

U.S. PATENT DOCUMENTS

| | | | |
|---|---|---|---|
| 3,852,362 | 12/1974 | Lambert | 424/222 |
| 3,973,129 | 8/1976 | Blumberg et al. | 250/458 |
| 4,328,163 | 5/1982 | Hanssle | 562/512 |

FOREIGN PATENT DOCUMENTS 9301310  12/1993  WIPO.

OTHER PUBLICATIONS

Wolff. C., Metodo Simplificado Para La Determinacion Del Acido Delta–Aminolevulinico Como Indicator Biologic De Intoxicacion Plumbica (abstract in English) pp. 226–230 vol. 102 No. 8 1974 Revista Medica De Chile.

Jordan, P. et al. Purification of Porphobilinogen Synthase from Bovine Liver pp. 427–434, vol. 123 (1986) Methods in Enzymology.

Bevan, D., et al Mechanism of Porphobilinogen Synthase, pp. 2030–2035 (1960) vol. 225 No. 5 Issued Mar. 10, The Journal of Biological Chemistry.

Pierce, J., et al Lead, Chromium, and Molybdenum by Atomic Absorption pp. 208–212 vol. 13 (Aug. 1966) Arch Environ Health.

Volosin, M. Use of Carbon Rod Atomizer for Analyse of Lead in Blood: Three Methods Compared, Clinical Chemistry vol.21, No. 13 1986–1987 (1975).

Anderson, P. et al. Purification and Properties of Aminolevulinate Dehydrase from Human Erthrocytes, pp. 6924–6930 vol. 254 No. 15, Issue of Aug. 10 (1979) The Division of Medical Genetics, Mount Sinai.

Sassa, S., Delta–Aminolevulinic Acid Dehydratase Assay vol. 28 pp. 133–145 (1982) Enzyme.

Gibbs, P., et al Purification and properties of 5–aminolaevulinate dehydratase from human erythrocytes Biochem J. 230, 25–34 (1985).

Berlin, A., European Standardized Method for the Determination of Aminolevulinic Acid Dehydratase Activity in Blood, pp. 389–390 (1974) Z. Klin Chem Klin Biochem.

Berlin et al, *Z. Klin. Chem. Klin. Biochem*, pp. 389–390, 1974.

Wolff, Revista Medica De Chile, (Abstract in English) vol. 102, No. 8, p. 226–230, 1974.

Volosin et al, *Clinical Chemistry*, vol. 21, No. 13, pp. 1986–1987, 1975.

*Primary Examiner*—Howard E. Schain
*Assistant Examiner*—Abdel A. Mohamed
*Attorney, Agent, or Firm*—David L. Weinstein

[57] ABSTRACT

Detection of lead present in a sample, comprising the steps of: (a) adding a lead recovery agent to an assay solution containing lead from the sample; (b) adding to the assay solution a disulfide enzyme which is inhibited in the presence of lead; and (c) correlating the activity of the disulfide enzyme to the amount of lead in the sample. The lead recovery agent enhances the sensitivity and accuracy of the assay such that the assay can be readily automated for detection of lead in whole blood using commercially available automation systems.

27 Claims, 5 Drawing Sheets

AUTOMATED LEAD ASSAY

This application is a continuation-in-part of U.S. Ser. No. 08/171,121 filed Dec. 21, 1993 and of U.S. Ser. No. 171,035 filed Dec. 21, 1993 both now abandoned.

BACKGROUND OF THE INVENTION

1. Field of the Invention

The present invention relates generally to assays for detecting lead in samples suspected of containing lead. More particularly, the invention concerns a lead assay capable of performing whole blood lead assays rapidly and easily on commercially available automated assay systems.

2. Background Discussion

The toxicity of lead is well-known. Trace amounts of lead can cause severe damage to human organs. Moreover, given the numerous and widespread sources of lead in the environment, the ability to rapidly detect even very low levels of lead in various human or environmental samples is becoming increasingly important to public health.

It is generally recognized that lead poisoning occurs in children at blood levels as low as 10–15 ug/dl. Lead contamination of environmental sources such as water, dust and soil requires identification at even lower levels. To measure these trace amounts, analytical techniques must be sensitive, contaminant-specific, and reliable Unfortunately, one well-known technique for accurately determining the presence of trace amounts of lead in a sample, a method known as atomic absorption, is both costly and time-consuming. Another well-known technique is anodic stripping voltametry. A drawback with this method is that it performs only one test at a time and usually involves the use of mercury compounds.

Another technique for determining the presence of lead involves the use of enzymes which are capable of being inhibited by lead. Enzymes are complex biological molecules which act as catalysts for various chemical reactions that occur in nature. One such enzyme, aminolevulinic acid dehydratase ("ALAD"), is inhibited in its effectiveness as a biological catalyst when exposed to lead. A known way to utilize this phenomenon to determine the presence of lead in a sample is to combine the sample suspected of containing lead with a mixture of ALAD and another compound known as aminolevulinic acid ("ALA"). ALA is a substrate for ALAD, meaning that ALAD will react with ALA. This reaction produces a reaction product called porphobilinogen ("PBG"). Under normal circumstances, when lead is not interfering with ALAD, the enzyme will convert its substrate ALA into PBG. However, when lead inhibits ALAD's ability to react with ALA, the reaction product PBG will not be formed, or will be formed in lesser amounts.

Thus, when a sample suspected of containing lead is mixed with ALAD and ALA, one can determine the presence of lead by observing whether and to what extent PBG is formed. If PBG production is reduced in a sample suspected of containing lead, this is an indication that lead is present in the sample and inhibiting the reaction between ALAD and ALA. In this enzyme-based test for lead, the presence of PBG is normally detected by using a coloring reagent which reacts with the PBG. After the PBG has been reacted with the coloring reagent, its presence can be determined colorimetrically—i.e. by transmitting light through the sample and measuring how the presence of the colored PBG affects the wavelength of light absorbed by the sample.

There are a number of problems which have prevented the ALAD-based technique discussed above from achieving widespread acceptance as a clinical test for lead. A principal problem is that the ALAD test is often not sensitive enough to detect the very low concentrations of lead in whole blood which are now generally regarded as toxic concentrations. For example, in an ALAD assay in which ALAD and ALA are added to a sample to detect potential inhibition by lead, the assay cannot be performed directly on whole blood. Instead, a blood sample usually is first treated with acid to release the lead from the red blood cells. The sample is then centrifuged to remove proteins and other materials which would interfere with the assay. The supernatant obtained after centrifugation must then be neutralized before ALAD and ALA can be added and incubated therein. Lead present in the blood sample tends to be poorly recovered as a result of these procedures such that it is either lost from the supernatant through precipitation, and the like, or is present in a form which is not readily accessable by the ALAD. Hence, analysis for porphobilinogen after ALAD and ALA are incubated in a whole blood supernatant may falsely indicate that the original whole blood sample does not contain a toxic level of lead. Absent a treatment method for blood samples in which all or essentially all of the lead in a blood sample can be isolated (i.e., recovered) into a supernatant of the blood in a form which can be detected by the ALAD assay, such assays directed to whole blood have serious limitations. To the best of our knowledge, it has heretofore been impossible to perform an ALAD-type assay for lead on a whole blood sample, much less one which is fully or partially automated, in such a manner that the results, in terms of concentration of lead detected, are comparable to the known methods of atomic absorption and anodic stripping voltametry.

Another difficulty associated with assays that use disulfide enzyme inhibition is that the enzyme must be activated, i.e. reduced, with a reducing agent. In known ALAD assays, the reducing agents are typically sulfhydryl compounds such as dithiothreitol. Unfortunately, these compounds interfere with color development of the porphobilinogen reaction product and hence must be precipitated from the assay solution. Known compounds typically used for effecting such precipitation are mercury salts which are unattractive from an environmental and toxicological standpoint. There is a pronounced need for alternatives to mercury salts. Ideally, it would be most desirable if a non mercury-based reducing agent could be discovered which would not need to be precipitated from the assay solution.

Yet another significant drawback in the ALAD assay is that it is labor intensive. To our knowledge, no one has succeeded in automating such an assay. Automation of the ALAD assay, especially for measuring lead concentration in whole blood, would be considered very attractive for clinical laboratories that require fast turnaround with lean staffing. Among the most popular automated analytical instruments currently employed in clinical laboratories worldwide are the IMx® Analyzer, the AxSYM® analyzer, the TDx® analyzer and the Vision® analyzer, all of which are manufactured by Abbott Laboratories. There exists a need in the art for a highly sensitive and accurate lead assay capable of being performed with little or no manual intervention on these types of computer-driven laboratory analyzers. It would be particularly advantageous to provide an automated enzyme-inhibition assay for lead in which the enzyme/substrate reaction product could be detected using the colorimetric or fluorometric detection systems which are found in commercially available analyzers such as the above-named instruments.

SUMMARY OF THE INVENTION

In a first method aspect, the present invention is an assay for detecting lead present in a sample of whole blood. The assay comprises the steps of (a) adding a lead recovery agent to a supernatant obtained from the blood sample, where the supernatant comprises the lead that was originally present in the blood sample; (b) adding to the supernatant a disulfide enzyme which is inhibited in the presence of lead; and (c) correlating the activity of the disulfide enzyme to the amount of lead in the blood sample. The assay exhibits sensitivity comparable to atomic absorption because the supernatant, by virtue of the lead recovery agent, contains all or substantially all (i.e. at least 90%) of the lead originally present in the whole blood sample in a form which is detectable in the assay such that the total amount of lead detected in the supernatant, as determined by step (c) of the assay, is at least 90%, and preferably at least 95%, of the total amount of lead capable of being detected in the sample of whole blood using the more cumbersome and costly technique of atomic absorption. The present invention makes it possible to automate the assay on commercially available laboratory analyzers.

In a related method, the invention is directed to an assay for detecting lead in a sample of whole blood, the assay comprising the steps of (i) adding an aminolevulinic acid dehydratase enzyme and aminolevulinic acid to an assay solution comprising a supernatant separated from the blood sample, wherein the supernatant, at the time of said addition, has a neutral pH and contains lead which was originally present in the whole blood sample; (ii) reacting said enzyme and amino acid under conditions sufficient to produce porphobilinogen; (iii) detecting the amount of porphobilinogen produced in said reaction; and (iv) correlating the amount of porphobilinogen with the amount of lead in the sample; and wherein the amount of lead detected in the supernatant as a result of steps (iii) and (iv) is at least 90% of the amount of lead which was present in the whole blood sample. The method is readily reduced to automation in view of the improvements disclosed herein. The lead detection sensitivity of the method is comparable to lead detection using atomic absorption in that the lead concentration detected by the present assay for a given blood sample is at least 90% of the concentration detected in the sample by atomic absorption, and preferably at least 95% of such concentration.

In a further method according to the invention, lead is detected in a sample suspected of containing lead by forming an assay solution in which there is combined a sample suspected of containing lead and an enzyme which is inhibited in the presence of lead, a substrate capable of reacting with the enzyme to form a reaction product, and a fluorescer (i.e., fluorophor) which does not react chemically with the enzyme, the substrate or the reaction product. This solution then is incubated under conditions sufficient to produce the reaction product. The incubated assay solution is then treated with a coloring reagent to convert the reaction product to a chromophore capable of providing a change in the transmitive properties of the assay solution within a wavelength band that overlaps the excitation and/or emission wavelength band of the fluorescer. After the coloring step, the assay solution is irradiated with light having a wavelength within the excitation wavelength band of the fluorescer, and the fluorescence emitted by the assay solution is then detected and measured as a means of measuring the concentration of lead in the sample. This method can be performed via automation on the Abbott Laboratories IMx®, TDx® and AxSYM analyzers with little or no equipment modifications.

The principal advantages of the present invention are elimination of precipitation steps; improved recovery (and hence detectability) of lead, particularly in a supernatant extracted from whole blood; the convenience of carrying out the assays on commercially available analyzers; and a surprising reduction in the extent to which trace metals interfere with the assay. Other benefits and advantages will become apparent hereinafter to persons skilled in the art.

DESCRIPTION OF THE INVENTION

Figure 1:
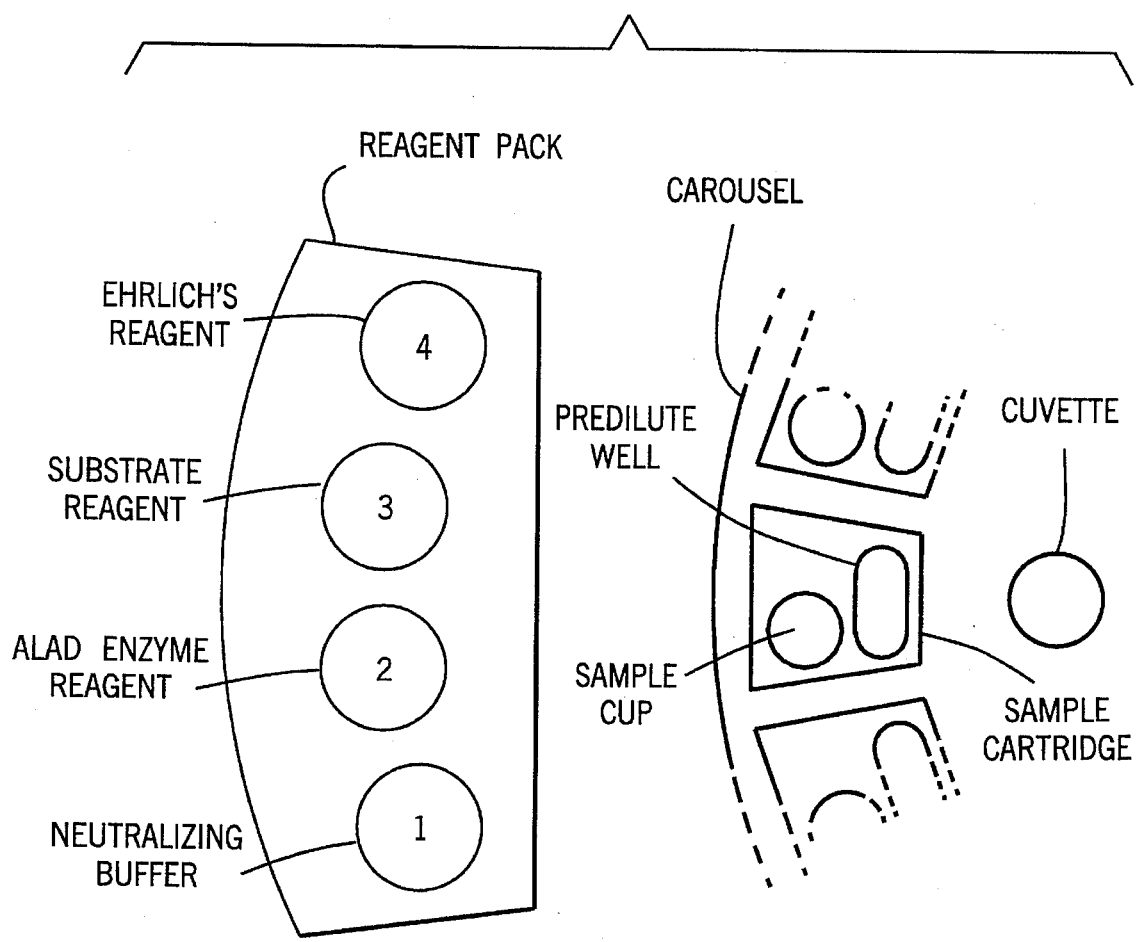
FIG. 1 is a schematic diagram of the Reagent Pack, Sample Carousel, and Cuvette for an IMx® Analyzer.

Generally speaking, the lead assay of the present invention involves reaction of a disulfide enzyme with a substrate in the presence of a sample suspected of containing lead. The enzyme and substrate selected are those which react to produce a detectable reaction product. The enzyme must be capable of inhibition by lead. The greater the concentration of lead in the sample, the less reaction product produced when the enzyme and substrate react. Conversely, as the amount of lead in the sample goes down, the amount of enzyme-substrate reaction product increases. By measuring the amount of the enzyme-substrate reaction product, one may indirectly measure the amount of lead in a sample. An enzyme and substrate combination suitable for use in the present invention is aminolevulinic acid dehydratase ("ALAD") and aminolevulinic acid ("ALA"). The detectable reaction product from this enzyme and substrate is porphobilinogen. Detection of the porphobilinogen is accomplished by coloring the compound with a suitable coloring agent to produce a chromophore. The chromophore is detected colorimetrically or fluorometrically. While the present invention can be used to detect lead in a variety of sample materials, the invention is particularly useful for automating a whole blood lead assay because it enables a sustantial improvement in the recoverability and detectability of lead from whole blood.

Briefly, a whole blood assay according to the present invention generally involves the following steps: First a supernatant of the whole blood is prepared by acidifying the blood to release lead from the red blood cells, followed by centrifugation to remove interfering substances. This step may be performed manually or via automation. The supernatant is then contacted with a lead recovery agent to enhance or maximize the extent to which any lead present in the supernatant is in a form which is acessible by the ALAD assay. After neutralization, disulfide enzyme and substrate are incubated in the supernatant in the presence of a reducing agent to produce a reaction product. The reaction product can be treated with a coloring agent or other appropriate label to facilitate detection. The amount of reaction product is then correlated to the amount of lead in the sample.

The enzyme activity in the assay solution can be measured in a number of ways by determining the amount of the substrate utilized or the PBG produced. Other reactants can be added to the sample solution for a subsequent reaction therewith. For example, an assay can be performed by competitively binding a suitable antibody to the PBG or to a fluorophore-PBG complex, and measuring the resultant fluorescent polarization level. Another example, as will be described further below, is a detection methodology which adds a fluorophore that is non-reactive in the assay and then measures the fluorescence quench caused by the colored reaction product of the enzyme/substrate reaction. In another example, an antibody which binds specifically to the substrate or to the product can be used in a suitable assay like ELISA, sandwich assay, agglutination assay, RIA and the like. Still another example is to label the substrate with a detectable characteristic and, subsequently, determine the extent the label is affected by the assay.

In accordance with the present invention, addition of the lead recovery agent, incubation of the enzyme and substrate, and detection of the reaction product are preferably carried out on a computer-driven laboratory analyzer.

The invention has several important features, each of which will be discussed in further detail below. First, the invention provides a sample pretreatment in which sample material suspected of containing lead is treated with an agent that combines or complexes with the lead to provide a substantial enhancement in the recovery of lead from the sample material. As used herein, the terms "recovered" and "recovery" denote that lead present in an original untreated sample is not lost (such as by precipitation and the like), and is not changed to a form which is poorly accessible to the ALAD enzyme, during sample preparation/separation steps necessary to perform the assay. Second, the invention provides a reducing agent for the enzyme (necessary for reaction between the enzyme and the substrate) which does not have to be precipitated prior to color development of the enzyme-substrate reaction product. This is particularly important because it eliminates a precipitation step that normally requires mercury compounds. Third, the invention affords enhanced color formation when the enzyme/substrate reaction product is reacted with a coloring agent to obtain a chromophore. Fourth, by conducting the assay in the presence of fluorescent compounds which do not interfere with the assay environment, the invention enables performance of the lead assay fluorometrically on commercially available automated laboratory analyzers which utilize fluorescence optics (e.g., the Abbott Laboratories IMx®, TDx®, and AxSYM® diagnostic instruments). While such fluorescence detection is preferred, the invention further provides a convenient automation of whole blood lead assays on the Abbott Vision® instrument using a colorimetric analysis of centrifugally mixed test cartridges containing preloaded assay reagents.

Improved Lead Recovery

The cornerstone of the present invention involves a pretreatment of a sample suspected of containing lead in a manner which enhances lead recovery therein. Increasing lead recovery in accordance with the invention enhances the sensitivity of lead assays which use enzyme inhibition. Enhancing lead recovery for an automated ALAD-based whole blood assay according to the present invention includes pretreating the sample to expose and recover the lead from within the red blood cells, and precipitating interfering compounds such as proteins, endogenous ALAD, and the like. Acid is commonly used to pretreat the sample. The interfering compounds are then pelleted by centrifugation leaving a blood supernatant which contains the lead isolated from the interfering compounds. This supernatant is the material on which the whole blood assay is conducted, hence it is critical that the steps in the assay necessary to prepare this supernatant for analysis do not result in loss of the recovered lead or its conversion to a form which is renders it poorly accessible by the disulfide enzyme.

Because the assay is performed at neutral pH, the acidified supernatant containing the recovered lead must be neutralized prior to incubation of the ALAD enzyme with ALA. A neutralizing reagent is therefore added to bring the supernatant sample to a neutral pH. Unfortunately, this required neutralization step causes lead present in the blood supernatant to become unavailable to the assay. During this neutralization step, it is therefore critical to the sensitivity and accuracy of the assay to maintain the lead present in the supernatant sample in an enzyme accessible form. The present invention achieves this by adding a lead recovery agent prior to or during the above-mentioned neutralization step. The lead recovery agent combines with the lead which has been isolated into the supernatant sample. When the recovery agent is present during neutralization of the acidified supernatant, the amount of recovered lead is substantially greater than when the agent is absent. Without being bound to any particular theory, we believe that the lead recovery agent of the present invention prevents loss of lead from the supernatant by preventing precipitation therefrom, or the like. Although the lead recovery agent combines with the lead in the supernatant, we have also made the surprising discovery that it makes the lead available for inhibiting the activity of the ALAD enzyme and does not diminish the activity of the ALAD enzyme.

Thus, as used herein, the term "lead recovery agent" means a reagent used according to the present invention to increase the detectability of lead in an assay sample in comparison to that achieved in the absence of the recovery agent, and which functions to bind with, or otherwise combine or chelate with the lead in a sample, while at the same time making the lead available for interaction with disulfide enzyme. The term "neutralizing reagent" or "neutralizing buffer" refers to the solution which brings the above-described acidified whole blood supernatant sample to a neutral pH. The lead recovery agents of the present invention enable the ALAD assay to achieve whole blood assay results which are comparable to the results obtained using atomic absorption. Specifically, in the present invention the amount of lead which can be detected by the whole blood ALAD assay is at least 90%, and preferably at least 95% of the amount of lead which can be detected in the same blood sample using atomic absorption.

The lead recovery agents used in the present invention include chelating agents capable of combining with the sample lead while still making the lead available to inhibit the activity of the ALAD enzyme. The currently preferred recovery agents for use with the present invention are lead chelating agents such as N-benzyliminodiacetic acid (BenzylIDA), L-histidine monohydrochloride monohydrate (Histidine), N-(2-hydroxyethyl)-iminodiacetic acid (HEIDA), iminodiacetic acid (IDA), DL-penicillamine (PEN), methyliminodiacetic acid (MIDA), nitrilotriacetic acid (NTA), sodium citrate, and 8-hydroxyquinoline-5-sulfonic acid hydrate (HQSA).

Lead recovery agents for use in the present invention further include compounds which form a complex with $Pb^{+2}$ as described by the $Pb^{+2}$ equilibrium binding constant (K) in the range of about 4 log K to about 13 log K. Particularly preferred are lead recovery agents exhibiting a $Pb^{+2}$ equilibrium binding constant in the range of about 6 log K to about 9 log K.

All the of the lead recovery agents identified above have a $Pb^{+2}$ equilibrium binding constant within the suitable range. Other lead recovery agents which exhibit a suitable $Pb^{+2}$ equilibrium binding constant include 8-hydroxy-5-(2'-hydroxyphenylazo) quinoline, 8-hydroxy-5-(phenylazo) quinoline, N-(2-carboxyphenyl)iminodiacetic acid, N-(acetonyl)iminodiacetic acid, N-(dithiocarboxy)aminoacetic acid, N,N-bis(2'-hydroxyethyl)glycine, and glycine.

Further lead recovery agents contemplated by the present invention include dihydroxyphenyl acetic acid, N-(2'-carboxyethyl)iminodiacetic acid, dihydroxybenzoic acid, 3,4, dihydroxybenzene sulfonic acid, melonic acid, 1-hydroxy-1-(3'-pyridyl)methane sulfonic acid, 4-aminopyridine-2,6-dicarboxylic acid, bathocuproinedisulfonic acid and bathophenanthrolinedisulfonic acid.

According to the present invention, the above-described lead recovery agents are used in an automated lead assay as follows: The sample suspected of containing lead is first treated in a conventional manner to isolate the lead into an aqueous solution so that the lead is separated from other compounds or substances originally in the untreated sample which may interfere with the lead assay. In the case of whole blood, this step can be accomplished in a conventional manner by adding trichloracetic acid, nitric acid, 5-sulfosalicylic acid, or perchloric acid to the whole blood sample. In the present invention, this initial sample treatment step may be carried out manually or as part of the automated assay.

Next, in instances where an acidified sample must be neutralized before the assay can continue with incubation of the enzyme and its substrate, the lead recovery agent is present in the sample during adjustment of the sample's pH to neutral. Although the present invention contemplates assays on whole blood samples which are pretreated by acidification to obtain a lead-containing aqueous supernatant, it will be appreciated that the neutralizing buffer is not required if an acidification step has not been used to isolate lead from the sample, or if the sample is otherwise at an appropriate pH for the assay. In such a case, the lead recovery agent should be present during any sample treatment steps which will have a tendency to cause lead originally present to be lost via precipitation and the like.

After the foregoing pretreatment step in which the sample has been contacted with the lead recovery agent, the assay continues by incubating the enzyme with the sample solution in the presence of a substrate. The enzyme incubation step is stopped after a predetermined time interval. In the case of ALAD and ALA, the product of the enzyme activity is porphobilinogen ("PBG"). By reacting PBG with a coloring reagent such as Erhlich's reagent to form a chromophore, one can photometrically determine the extent of the enzyme activity. Other coloring reagents containing dimethylaminobenzaldehyde, dimethylaminocinnamaldehyde or their derivatives are suitable for use with the present invention. As will be explained further below, the chromophore may also be detected fluorometrically.

A further substantial advantage in using the lead recovery agents of the present invention is the ability to obtain a marked reduction in interference from other metals which may be present in the assay solution. The table shown below reports the results of our investigations of metal interference in the assay of the present invention conducted on an IMx® analyzer. In these investigations the lead recovery agent used was 8-hydroxyquinoline-5-sulfonic acid hydrate (HQSA). As shown in the table, the listed metals, when present in their normal concentrations in blood and serum, do not interfere with an ALAD-based assay according to the present invention.

| METAL INTERFERENCE IN THE IMx LEAD ASSAY | | |
|---|---|---|
| Metal | Normal Range Concentration | Interfering Conc. ($>\pm$ 2 St. Dev.'s) in the present invention |
| Al | 0.04–0.52 µM | (serum) 10 mM |
| Ba | ≤2.9 µM (whole blood) | 10 mM |
| Ca | 2.1–2.8 mM (serum) | 25 mM |
| Cd | 0.9–44.5 nM (whole Blood) | 10 mM |
| Co | 1.9–7.6 nM (serum) | 10 mM |
| Cr | 54–864 nM (whole blood) | 10 mM |
| Cu | 11–30 µM (serum) | 500 µM |
| Fe | 9–31 µM (serum) | 10 mM |
| Hg | 3–294 nM (whole blood) | 10 mM |
| Mg | 0.7–1.1 mM (serum) | 100 mM |
| Mn | 140–220 nM (whole blood) | 10 mM |
| Ni | 17–476 (whole blood) | 10 mM |
| Sn | <664 nM (serum) | 10 mM |
| Tl | <24.5 nM (whole blood) | 10 mM |
| Zn | 11–23 µM (serum) | 100 µM |

Enhancement Using Tertiary Phosphines

Another aspect of the present invention concerns a reducing agent used to activate the enzyme substrate reaction. While it is known that reaction between ALAD and ALA requires a reducing agent, a known reducing agent for this purpose, dithiothreitol (DTT), interferes with color formation when the reaction product PBG is colored with a coloring agent. This problem is typically addressed by reacting the DTT with a mercury salt (mercuric chloride). Mercury forms a precipitate with the DTT which can be removed from the assay solution by centrifugation or the like.

We have discovered a new class of reducing agents, suitable as replacements for DTT, which do not interfere with the PBG color development, and hence do not have to be precipitated from the incubated assay solution. In particular, we have discovered that water-soluble tertiary phosphines can be used to enhance the reaction between disulfide enzymes and their substrates in the assay of the present invention. We believe that the tertiary phosphines reduce the disulfide bonds of the enzyme to enhance or increase the activity of the enzyme. Unlike sulfhydryl compounds (e.g., dithiothreitol) we have found that these compounds do not interfere with the color formation step of the assay and therefore do not need to be precipitated prior to color formation.

A preferred water-soluble tertiary phosphine is tris(2-carboxyethyl)phosphine (TCEP). Other suitable tertiary phosphines include tributylphosphine, tris(4-carboxyphenyl)phosphine and tris(hydroxymethyl)phosphine. The effect of the inventive activating reagents is apparent at very low concentrations. A preferred concentration for using the water-soluble tertiary phosphine is greater than about 0.5 mM in the enzyme reagent. Above this concentration the improvement levels off.

Enhanced Color Formation

A further feature of the present invention involves the use of color enhancing agents which we have found can be substituted for mercuric ion in either the stop reagent or the colorant solution or both. A preferred color enhancing agent comprises the cupric ion $Cu^{+2}$. Any compound which contains the cupric ion is suitable for use in the present invention provided it does not detract from any other aspects of the assay chemistry. When an automated assay according to the present invention uses sulfhydryl reducing agents compounds (such as DTT), we have discovered that precipitation of the sulfhydryl compounds is accomplished when the cupric ion is present, and that mercury compounds can thus be eliminated from the assay. Moreover, the sensitivity and accuracy of the assay is improved over assays which employ mercury compounds to precipitate the sulfhydryl reducing agents.

When cupric ion is used in combination with the tertiary phosphines discussed above, we have found that color enhancement is improved over (a) use of the tertiary phosphine alone or (b) use of sulfhydryl compounds with mercury precipitation. A suitable concentration range for the cupric ion is about 1 mM to about 500 mM in the assay solution.

Another inventive colorimetric enhancing reagent contemplated by the present invention is the ferric ion and any compound which contains the ferric ion is suitable for use by the present invention. When the ALAD assay is conducted with a sulfhydryl reducing agent, we have found that replacing mercuric chloride with ferric chloride affords an assay with comparable sensitivity to known ALAD assays which use mercuric chloride to precipitate the sulfhydryl compounds. The ferric ion is preferably used in combination with a sulfhydryl compound like DTT. A preferred concentration range for the ferric ion is about 1 mM to about 500 mM in the assay solution.

The ferric or cupric compounds can be added to the sample solution prior to photometrically determining the extent of the incubation reaction. The addition can take place while adding the stopping reagent or a coloring reagent or both.

In any automation procedure in which there is a potential for contamination by the copper or iron in other assay reagents, the copper and iron may be eliminated without affecting the benefits afforded by the other features of the invention as described herein. In such case, the peformance of the assay will still be markedly superior to prior art ALAD-type lead assays.

Assay Automation

The present invention enables performance of an enzyme inhibition assay on automated analyzers that are commercially available. One such analyzer is the popular IMx® benchtop analyzer sold by Abbott Laboratories. The IMx® benchtop analyzer is described in Clinical Chemistry, Vol. 34 No. 9, pages 1726–1732, which is incorporated herein by reference. This instrument, as well as its method of use are exceedingly well known in the art. Briefly, the IMx® instrument is a microprocessor-based analyzer which uses a robotic pipetting arm in combination with a rotating sample carousel and a reagent pack to carry out batch processing of one assay on each of a plurality of samples placed in the carousel. The automated lead assay of the present invention, as performed on the IMx®, uses the instrument's fluorescense optics. However, unlike competitive assays conventionally performed on the IMx®, the lead assay described herein is neither an immunoassay, nor does it measure changes in polarization based on binding of an anlayte-tracer to an antibody. Instead, the present invention is based on our discovery that a highly sensitive lead assay measuring the enzyme-substrate reaction of a disulfide enzyme may be automated for the IMx® instrument by conducting the assay in the presence of a fluorescent compound which does not react with the other assay reagents. In one such assay according to the invention, the reaction between ALAD and ALA produces a reaction product (porphobilinogen) which, when contacted with a coloring agent such as Ehrlich's reagent, produces a chromofore (i.e. a colored reaction product). The presence of this chromophore in the assay reaction mixture changes the color of the mixture, and thus reduces the net intensity of the fluorescent light emitted by the fluorescent compound present in the reaction mixture. This change in the intensity of the light transmitted by the fluorescent compound can be correlated to the amount of PBG produced in the assay, and hence to the amount of lead present in the sample. For example, reaction of ALAD and ALA in a sample containing no lead will produce a given level of PBG. When colored with Ehrlich's reagent, this PBG will change the transmittive properties of the sample and cause a quantifiable reduction in the net fluorescence intensity emitted by the fluorescent compound present in the sample. For purposes of discussion, the absolute value of this reduction in net intensity may be taken as "X" units. As lead concentration increases, PBG production decreases causing a decrease in the value of X. Using an appropriate standard curve on known lead standard solutions, one can plot the amount of lead against the value of X.

In particular, after the coloring step in which porphobilinogen is reacted with a coloring agent, the assay solution is irradiated with light having a wavelength within the excitation wavelength band of the fluorescer, and the fluorescence emitted by the assay solution is then detected and measured as a means of measuring the concentration of lead in the assay reaction mixture. The term "fluorescer" is intended to have the same meaning as used in commonly assigned Shaffar U.S. Pat. No. 4,495,293. While this type of fluorometric analysis has been disclosed for a variety of assays in the '293 patent (incorporated herein by reference), to our knowledge no one has succeeded in developing an automated, highly sensitive fluorometric ALAD lead assay, much less one that can be easily performed on existing laboratory analyzers without costly equipment modifications. We have discovered that dyes in the rhodamine family are particularly well-suited for performing this type of fluorometric analysis. Other dyes may be used provided they are compatible with the pH and other conditions of the assay solution.

It will be appreciated that the type of fluorometric analysis generally described above can also be performed on the Abbott TDx® instrument as well as the Abbott AxSYM® instrument. The principles of the TDx® analyzer are well known in the art and are disclosed, e.g., in Clinical Chemistry. Vol. 27, No. 9, p 1575 (1981) incorporated herein by reference. The AxSYM® random and continuous access analyzer is the subject of recently issued commonly-assigned U.S. Pat. No. 5,358,691 to Clark et al. and is also described in Clinical Chemistry, Vol. 39, No. 10, p. 2063 (1993) both of which are incorporated by reference herein. All of the reagents necessary for performing the lead assay of the present invention can be automatically pre-kitted on the sample carousel of the AxSYM® analyzer in the preprogrammed manner generally described in the '691 patent.

Yet another analytical instrument on which the lead assay of the present invention can be conveniently automated is the Abbott Laboratories Vision® analyzer. The Vision® benchtop analyzer is well-known in the art and the full details of its operation are disclosed in Clinical Instrument Systems, Vol. 10, No. 3 (1989) and in commonly assigned U.S. Pat. No. 4,883,763 to Holen et al., both of which are incorporated herein by reference. Briefly, the Vision® analyzer comprises a centrifuge platter on which are placed a number of test cartridges. A Vision® test cartridge suitable for use in the present invention is shown schematically in FIG. 3 hereof. Each test cartridge is pre-loaded with reagents necessary to perform a desired assay. The test cartridges are equipped with an arrangement of mixing channels and mixing chambers. One or more of these chambers contain the pre-loaded reagents. The operator of the instrument must place a sample (such as blood) into a sample well of the test cartridge and then load the cartridge onto the centrifugal platter of the Vision® analyzer. When the centrifuge platter begins to rotate, centrifugal force causes the reagents to be released from the pre-filled chambers of each test cartridge and transferred into the cartridges various mixing chambers. At the same time, centrifugal force causes the sample loaded by the operator to be forced into a separate mixing chamber. The mixing chambers of the test cartridge are designed to hold a pre-determined quantity of sample and reagent, with excess liquids being forced into overflow chambers. After an initial period of centrifugation in what is termed the "install" position (i.e. the position in which the test cartridges are placed onto the centrifuge platter) each test pack is then automatically rotated 90° counterclockwise to the "mix" position causing two or more of the pre-loaded reagents to mix in a predetermined manner based on the precise configuration of the mixing channels in the cartridge. The cartridges are then automatically rotated clockwise 90° to return the cartridge to the install position. This cycle of rotations known as a mix-install cycle is carried out one or more times until the sample and reagents are mixed and transferred to a final transparent cuvette region of the cartridge (labelled H in FIG. 3) from which the assay reaction mixture can be analyzed by the Vision® photometric assembly.

EXAMPLE 1

The Use of Lead Recovery Agents

All the reagents used in the present example are available commercially. The aminolevulinic acid (ALA) and d-aminolevulinic acid dehydratase (ALAD) were both purchased from Sigma Company of St Louis, Mo., as cat. nos. A-3785 and A-0644, respectively. The $HgCl_2$, dimethylaminobenzaldehyde (DMAB) and dithiothreitol are also available from Sigma as cat. nos. M-6529, D-8904 and D-0632. The buffer (bis[2-hydroxyethyl]imino-tris[hydroxymethyl]methane (Bis-Tris), concentrated $HNO_3$ acid, NaOH pellets, $ZnCl_2$ (99+% pure), and trichloroacetic acid (TCA) are available from Aldrich Chemical Company of Milwaukee, Wis., as cat. nos. 15,666-3, 22,571-1, 30,657-6, 22,999-7, and 25,139-9. The 10 mg/dl lead standard was also purchased from Aldrich as cat. no. 31,902-3. The glacial acetic acid and 60% perchloric acid were purchased from Fisher as cat. nos. A38-212 and A228-1

The lead recovery agents tested include: N-benzyliminodiacetic acid (BenzylIDA) purchased from Aldrich as cat. no. B2,475-8 (98% pure); ethylenebis (oxyethyleneni trilo)tetraacetic acid (EGTA) Aldrich cat. no. 23,453-2 (97% pure); ethylenediaminetetraacetic acid (EDTA) purchased from Sigma cat. no. ED2P (98% pure); L-histidine monohydrochloride monohydrate (Histidine) purchased as Aldrich cat. no. H1,520-9 (98% pure); N-(2-hydroxyethyl)iminodiacetic acid (HEIDA) purchased as Aldrich cat no. 15,814-3 (98% pure); Iminodiacetic Acid (IDA) purchased from Aldrich cat. no. I-120-0 (97% pure); DL-penicillamine (PEN) purchased from Aldrich cat. no. P60-8 (99+% pure); methyliminodiacetic acid (MIDA) purchased from Aldrich cat. no. M5,100-8 (99% pure); nitrilotriacetic acid (NTA) purchased from Aldrich cat no. 10,629-1 (99+% pure); sodium citrate purchased from Mallinckrodt cat. no. 0754 (99.7% pure); 8-hydroxyquinoline-5-sulfonic acid hydrate (HQSA) purchased from Aldrich cat. no. H5,875-7 (98% pure).

The spectrophotometer used for absorbance measurements is a LKB Ultraspec II Model 4050.

Method

All flasks used in the preparation of solutions described herein were washed with 1N $HNO_3$ The solutions prepared were stored at room temperature unless otherwise noted. The pH of 50 ml of HPLC grade distilled water was adjusted to pH 1.50 by adding an appropriate amount of concentrated $HNO_3$. A 20 mM $ZnCl_2$ solution was prepared by adding pH 1.50 distilled water to 0.0340 g $ZnCl_2$ for a final solution weight of 12.500 g. The solution was then thoroughly mixed.

A solution of 200 ml 1.5M Bis-Tris was prepared by adding 62.70 g of Bis-Tris to HPLC grade distilled water to a final volume of about 180 ml. After stirring, the pH was adjusted to 7.30 with concentrated $HNO_3$. The resulting volume was adjusted to the mark with distilled water. Similarly a 200 ml solution of 2.0M Bis-Tris was prepared by using 83.60 g of Bis-Tris. The pH was adjusted to pH 7.60 before adjusting the volume. Both Bis-Tris solutions were stirred for 10 min. at room temperature and filtered to remove any visible particles.

A diluted enzyme reagent was prepared by adding 5 ml of ALAD containing 3.1 U/mg to 35 ml of 250 mM Bis-Tris. The 250 mM Bis-Tris diluent solution was prepared by adding 5.23 g. Bis-Tris to 100 ml of HPLC grade distilled water and stirring. DTT was added to 10 mM in the diluted enzyme reagent. Other sulfhydryl compounds such as glutathione, mercaptoethanol and cysteine can be used as a reducing agent instead of DTT. The pH of the diluent solution was adjusted to pH 7.0 by adding 50% NaOH. The diluted enzyme reagent was stored at 2°–8° C. under nitrogen gas.

A 25 mM ALA and 10 μM $ZnCl_2$ substrate solution was prepared by adding 0.210 g. ALA, 25 μl 20 mM $ZnCl_2$ and 50 ml HPLC distilled water to a flask. After stirring, the substrate solution was stored at 2.8° C. in the dark.

A stop reagent containing 10% TCA was prepared by adding 20.000 g of TCA, 0.1M $HgCl_2$ and HPLC grade distilled water to 200 ml. The solution was stirred and filtered at 0.80 um.

A pretreatment reagent containing 17.5% TCA was prepared by adding 17.5 g TCA to 100 ml HPLC distilled water and stirring.

A modified Ehrlich's Reagent was prepared by adding 12.5 g DMAB, 250 ml glacial acetic acid and 122.5 ml of 60% perchloric acid and mixing. The final volume was adjusted to 500 ml by adding more glacial acetic acid. The modified Ehrlich's Reagent was stored in the dark at 2°–8° C.

A whole blood mixture was prepared by collecting 180 ml of whole blood from type B+ and O+ donors and adding 20 mg of sodium heparin. A test sample containing 40 ug/dl $Pb^{+2}$ was prepared by adding 0.320 g of 10 mg/dl $Pb^{+2}$ to 80.0 ml of the whole blood mixture. The remainder of the whole blood mixture was used as a control containing 0

μg/dl of $Pb^{+2}$. After vigorous mixing, both test samples were stored for 4 hours with mixing every 30 min., and subsequently, overnight at 2°–8° C.

For each lead recovery agent, a neutralizing solution containing 0.5M of the agent and 1.5M Bis-Tris was prepared by adding 7.5 ml of the 2M Bis-Tris solution to following amounts of recovery agents: Na Citrate 1.470 gm; IDA 0.975 g; NTA 1.175 g; EGTA 1.900 g; Histidine 1.050 g; HEIDA 0.885 g; MIDA 0.735 g; BenzylIDA 1.115 g; HQSA 1.125 g; EDTA 1.840 g; and PEN 0.745 g. After stirring, HPLC grade distilled water was added to each neutralizing solution to obtain a final volume of about 9.5 ml. Subsequently, the recovery agent solutions were vigorously stirred overnight. The neutralizing solutions containing Histidine, HQSA and PEN were heated to about 70° C. to complete dissolution and then cooled to room temperature. The pH of each neutralizing solution was then adjusted to pH 7.25 with either concentrated HNO3 or 50% NaOH.

Whole blood samples containing 0 μg/dl and 40 μg/dl $Pb^{+2}$ were dispensed in 24.5 ml amounts and were pretreated with 10.5 ml of the TCA pretreatment solution.

Each sample was centrifuged for five minutes and the supernatants were saved. From each supernatant solution 180 μl was mixed by vortex with 180 μl of neutralizing buffer. From this neutralized supernatant solution 100 ul was added to 100 μl of the dilute enzyme reagent and mixed by vortex and incubated for 15 min in a 37° C. water bath.

Subsequently 100 μl of the substrate solution was added, mixed by vortex and incubated for 30 min. in the water bath. The stop reagent was added in an amount of 250 μl and mixed by vortex. The mixture was centrifuged for two minutes to remove insoluble DTT.

The supernatant mixture was removed and added to 500 μl of the modified Ehrlich's reagent. After mixing by vortex and incubating for 10 min. at room temperature, the absorbance was recorded at 555 nm.

Results

The absorbance data for each lead recovery agent was collected at the following concentrations, measured in mM after being mixed with the pretreated whole blood supernatant: 0.25, 1.00, 2.50, 10.00, 25.00, 100.00 and 250.00. Table 1 shows the measured absorbance span difference for each lead recovery agent in the samples containing 0 μg/dl and 40 μg/dl $Pb^{+2}$. The equilibrium constant of $Pb^{+2}$ for each lead recovery agent (as reported in the literature) is included in Table 1.

TABLE 1

| Recovery Agent | Conc. mM | Absorbance Span | $Pb^{+2}$ Equilibrium Constant |
|---|---|---|---|
| Control | — | 0.006 | — |
| Na Citrate | 250.00 | 0.106 | 4.3 |
| Histidine | 250.00 | 0.915 | 6.4 |
| IDA | 250.00 | 0.801 | 7.5 |
| MIDA | 100.00 | 0.735 | 8.0 |
| HQSA | 2.5 | 0.891 | 8.5 |
| HEIDA | 250.00 | 0.223 | 9.5 |
| NTA | 10.00 | 0.110 | 11.6 |
| PENICILLAMINE | 100.00 | 0.311 | 13.0 |
| EGTA | 10.00 | 0.016 | 14.7 |

EXAMPLE 2

The Use of Tertiary Phosphine

Materials

All the reagents used in the present invention are available commercially. The aminolevulinic acid (ALA) and d-aminolevulinic acid dehydratase (ALAD) are both purchased from Sigma Company of St Louis, Mo., as cat. nos. A-3785 and A-0644, respectively. The $HgCl_2$, dimethylaminobenzaldehyde (DMAB), dithiothreitol (DTT), and trichloroacetic acid (TCA) are also available from Sigma as cat. nos. M-6529, D-8904, D-0632, and T-6399. The buffer (bis[2-hydroxyethyl]imino-tris[hydroxymethyl]methane (Bis-Tris) is available from Aldrich Chemical Company of Milwaukee, Wis., as cat. no. 15,666-3. The glacial acetic acid, 60% perchloric acid and concentrated $HNO_3$ acid is purchased from Fisher as cat. nos. A38-212, A228-1, and A200-212. The L-histidine monohydrochloride monohydrate (Histidine) and Iminodiacetic Acid (IDA) is available from Aldrich as cat. nos. H1,520-9 and I-120-0, respectively. The 10 mg/dl $Pb^{+2}$ volumetric standard is also purchased from Aldrich as cat. no. 31,903-3. The $ZnCl_2$ is purchased from Mallinckrodt as cat. no. 8780.

The $FeCl_3$ and the $CuCl_2\text{-}2H2O$ are purchased from Aldrich as cat nos. 23,648-9 and 30,748-3. The reducing agent Tris(2-carboxyethyl)phosphine Hydrochloride (TCEP-HCL) is obtained from Pierce as cat. no. 20490

The spectrophotometer used for absorbance measurements is a LKB Ultraspec II Model 4050.

Method

The solutions prepared are stored at room temperature unless otherwise noted. The pH of 50 ml of HPLC grade distilled water is adjusted to a pH 1.50 by adding an appropriate amount of concentrated HNO3. The pH 1.50 distilled water is then added to 0.0340 g. $ZnCl_2$ for a final solution weight of 12.500 g. The solution is then thoroughly mixed.

A neutralizing solution containing 0.5M IDA, 0.125M Histidine and 1.5M Bis-Tris is prepared by adding 7.5 ml of a 2M Bis-Tris solution to following amounts of IDA 0.975 g and Histidine 1.050 g. After stirring, HPLC grade distilled water is added to the neutralizing solution to obtain a final volume of about 9.5 ml. A solution of 200 ml 2M Bis-Tris was prepared by adding 83.60 g of Bis-Tris to HPLC grade distilled water to a final volume of about 180 ml. After stirring, the pH is adjusted to 7.11 with concentrated $HNO_3$. The resulting volume is adjusted to 200 ml with distilled water. The Bis-Tris solution is stirred for 10 min. at room temperature and filtered to remove any visible particles.

A diluted enzyme reagent is prepared by adding 5 ml of ALAD containing 3.1 U/mg to 35 ml of 250 mM Bis-Tris. The 250 mM Bis-Tris diluent solution is prepared by adding 5.23 g Bis-Tris to 100 ml of HPLC grade distilled water and stirring. DTT is added to 15 mM in the diluted enzyme reagent. The pH of the diluent solution is adjusted to pH 7.0 by adding 50% NaOH. The diluted enzyme reagent is stored at 2°–8° C. under nitrogen gas.

A 25 mM ALA and 10 μM $ZnCl_2$ substrate solution is prepared by adding 0.0127 g. ALA, 30 ul 1 mM $ZnCl_2$ and 3 ml HPLC distilled water to a flask. After stirring, the substrate solution is stored at 2.8° C. in the dark.

A stop reagent containing 10% TCA is prepared by adding 20.000 g of TCA, 0.1M $HgCl_2$ and HPLC grade distilled water to 200 ml. The solution is stirred and filtered at 0.80 μm. The various concentrations reported in Table 1 below are prepared by serial dilutions.

For comparison, two inventive stop reagents were prepared by respectively substituting 27 mg of $FeCl_3$ and 26.8 mg of $CuCl_2$ for the $HgCl_2$ and adding HPLC grade distilled water to a total volume of 2 ml. The various concentrations reported in Table 2 below are prepared by serial dilutions.

A modified Ehrlich's Reagent is prepared by adding 12.5 g DMAB, 250 ml glacial acetic acid and 122.5 ml of 60% perchloric acid and mixing. The final volume is adjusted to 500 ml by adding more glacial acetic acid. The modified Ehrlich's Reagent is stored in the dark at 2°–8° C.

A 40 μg/dl $Pb^{+2}$ water sample is prepared by dilution of the 0.1 mg/ml lead standard from Aldrich. This dilution was performed with a standard HPLC water that had been pH adjusted to 1.9 with $HNO_3$. The pH 1.9 water served as the 0 μg/dl sample. These water samples were neutralized with the neutralizing buffer to pH 7.0. The ratio of the water samples to neutralizing buffer was 60/40.

The assay is run by adding 100 ul of the neutralized water samples to individual polystyrene tubes. The enzyme reagent is added in 100 μl amounts and incubated for 5 minutes at 37° C.

Subsequently 100 μl of the substrate solution is added, mixed by vortexing and incubated for 25 min. in the water bath. The stop reagent is added in an amount of 200 μl and mixed by vortexing. The mixture is centrifuged for two minutes to remove insoluble DTT.

The supernatant mixture is removed and added to 500 ul of the modified Ehrlich's reagent. After incubating for 5 min. at room temperature, the absorbance of the supernatant is recorded at 555 nm.

Results

The absorbance data for each metal ion, $Hg^{+2}$, $Cu^{+2}$, and $Fe^{+3}$, is collected at various concentrations measured in mM. Table 1 shows the measured absorbance at 555 nm. averaged over several trials for each metal ion in the samples containing 0 μg/dl $Pb^{+2}$.

Although all three metal ions give an increased signal intensity, the effect levels off before a concentration of about 100 mM is reached for the $Hg^{+2}$ and $Fe^{+3}$ metal ions. The $Cu^{+2}$ metal ion, however, continued to increase the signal intensity beyond the 100 mM concentration level. Accordingly, the procedure was continued at higher concentrations as reported in Table 2.

TABLE 2

| Conc. mM | Average Absorbance at 555 nm | | |
|---|---|---|---|
| | $Cu^{+2}$ | $Fe^{+3}$ | $Hg^{+2}$ |
| 1.0 | 0.696 | 0.650 | 0.500 |
| 5.0 | 1.309 | 0.717 | 1.143 |
| 10.0 | 1.783 | 0.800 | 1.845 |
| 20.0 | 1.782 | 1.177 | 1.840 |
| 50.0 | 1.854 | 1.797 | 1.826 |
| 100.0 | 1.977 | 1.823 | 1.808 |
| 200 | 2.059 | | |
| 300 | 2.192 | | |
| 400 | 2.281 | | |
| 500 | 2.297 | | |

Other metals, including ferrous chloride $FeCl_2$, were tested according to the procedure set forth above. The ferrous chloride, which contains the $Fe^{+2}$ ion, reported an absorbance of only 0.534 at a concentration of 100 mM which was not significantly different than results with no added metal.

EXAMPLE 3

Method

In this example, the same procedure described in Example 2 is used to compare the metal ions using a water soluble tertiary phosphine, TCEP, as a substitute for the reducing agent DTT. The diluted enzyme reagent is prepared as previously described except that TCEP is added to 5 mM in the diluted enzyme reagent instead of the DTT.

Results

The absorbance data for each metal ion, $Hg^{+2}$, $Cu^{+2}$, and $Fe^{+3}$, is collected at various concentrations measured in mM using TCEP rather than DTT in the enzyme reagent. Table 3 shows the measured absorbance span difference for each metal ion between the samples containing 0 μg/dl and 40 μg/dl $Pb^{+2}$. To determine if the effect of $Cu^{+2}$ on signal intensity observed in Example 2 would also be demonstrated using TCEP, the procedure is continued at higher concentrations for the metal ions $Cu^{+2}$ and $Fe^{+3}$ is reported in Table 3. Table 3 also shows an increased absorbance span with $Cu^{+2}$ over $Hg^{+2}$ and $Fe^{+3}$.

TABLE 3

| Conc. mM | Absorbance Span with TCEP | | |
|---|---|---|---|
| | $Cu^{+2}$ | $Fe^{+3}$ | $Hg^{+2}$ |
| 10.0 | 0.978 | 1.053 | 0.915 |
| 20.0 | 0.874 | 1.070 | 0.915 |
| 50.00 | 0.978 | 1.034 | 0.994 |
| 100.0 | 1.066 | 1.091 | 1.020 |
| 200 | 1.250 | 1.125 | |
| 500 | 1.480 | 1.149 | |

EXAMPLE 4

Method

In this example, the same procedure described in Example 2 is used to prepare an enzyme reagent with DTT and a stop reagent with and without $CuCl_2$. As in Example 3, a diluted enzyme reagent is prepared using TCEP added to 5 mM. The same stop reagents with and without $CuCl_2$ are used to compare the effect of DTT and TCEP on the sensitivity of the assay.

Results

The absorbance data for the metal ion $Cu^{+2}$ is collected at concentrations of zero and 400 mM comparing the use of TCEP and DTT in the enzyme reagent. Table 4 shows the measured absorbance span for both concentrations of the metal ion between the samples containing 0 μg/dl and 40 μg/dl $Pb^{+2}$. The use of TCEP provides a significant enhancement of the signal intensity even when the metal ion is eliminated.

TABLE 4

| $CuCl_2$ Conc. mM | Absorbance Span | |
|---|---|---|
| | DTT | TCEP |
| None | 0.476 | 1.045 |
| 400 | 1.490 | 1.458 |

EXAMPLE 5

IMx® Lead Assay Standard Curve

An automated lead assay according to the present invention is performed on an Abbott Laboratories IMx® analyzer as follows to obtain a standard curve:

Materials

All reagents used are available commercially. The d-aminolevulinic acid (ALA), d-aminolevulinic acid dehydratase (ALAD), and 4-dimethylaminobenzaldehyde (DMAB) are obtained from Sigma Company of St. Louis, Mo., as cat. nos. A-3785, A-0644 and D-8904, respectively. From Aldrich Chemical Company is obtained 2,2-bis(hydroxymethyl)-2,2'2"-nitrilotriethanol (Bis-Tris), citric acid, 8-hydroxyquinalone-5-sulfonic acid (HQSA), zinc chloride, copper (II) chloride dihydrate, and a 10 mg/dL lead volumetric standard as cat. nos. 15,666-3, 25,127-5, H5,875-7, 22,571-1, 30,748-3 and 31,902-3, respectively. Tris(2-carboxyethyl)-phosphine (TCEP) is obtained from Pierce, Rockford, Ill. as cat. no. 20490. Rhodamine 110 is obtained from Eastman Kodak, Rochester, N.Y. as cat. no. 1361468. Glacial acetic acid is obtained from Mallinckrodt, Paris, Ky. as cat. no. V194. Concentrated hydrochloric acid (HCl) is obtained from Baker, Phillipsburg, N.J. as cat. no. 9535-3. HPLC grade water is obtained from EM Science, Gibbstown, N.J., as cat. no. WX0004-1. TDx® buffer (0.1M phosphate with 0.1% sodium azide) is obtained from Abbott Laboratories.

Reagent Solutions

The following solutions are prepared:

Aqueous lead standards at 0, 7, 14, 21, 28 and 42 µg/dL were prepared by gravimetric dilution from a 10 mg/dL stock lead solution into an aqueous solution of 75 mM citric acid adjusted to pH 0.95.

A 1.5M Bis-Tris solution in HPLC distilled water is prepared and adjusted to pH 7.3 with concentrated $HNO_3$. The solution was filtered to remove particulates and maintained at room temperature.

A stock solution of 100 mM HQSA in the 1.5M Bis-Tris solution is prepared and adjusted to pH 7.25.

ALAD enzyme diluent is 0.15M Bis-Tris adjusted to pH 6.7.

From the foregoing solutions, the following reagent solutions are prepared:

1. Neutralizing Buffer. Neutralizing buffer was prepared by adding 10 ml of the above 100 mM HQSA stock solution to 90 ml of the 1.5M Bis-Tris solution. The pH is adjusted to 7.30 and the solution is maintained at room temperature. The neutralizing buffer is placed in the first reagent well of an IMx® reagent pack as illustrated in FIG. 1.

2. ALAD Enzyme Reagent. ALAD enzyme reagent is prepared by diluting one part 3.1 U/mg ALAD solution into 3 parts 150 mM Bis-Tris solution then adding Rhodamine 110 to a final concentration of 5 µM. The ALAD enzyme reagent is placed in the second reagent well of the IMx® reagent pack as shown in FIG. 1.

3. Substrate Reagent. A substrate solution in HPLC distilled water is prepared containing 40 mM ALA, 20 µm ZnCl, and 20 mM TCEP and 5 µM Rhodamine 110. The Substrate reagent is placed in the third reagent well of the IMx reagent pack as shown in FIG. 1.

4. Ehrlich's Reagent. Ehrlich's reagent is prepared with 0.67M DMAB and 0.40M copper (II) chloride in a 50:50 mixture of glacial acetic acid and conc. HCl. The Ehrlich's reagent is placed in the fourth reagent well of the IMx reagent pack as shown in FIG. 1.

Method

FIG. 1 schematically illustrates the reagent configuration used for the Lead assay of the present invention as performed on the IMx® instrument. The reagent pack identified in FIG. 1 corresponds to the reagent pack of a commercially available IMx analyzer. The carousel shown in FIG. 1 represents a known type of carousel commercially used on the IMx instrument for conducting fluorescence polarization immunoassays. As shown in FIG. 1, each position on the carousel contains a sample cartridge having a sample cup and predilute well and a cuvette. The sample cartridge, although shown schematically in FIG. 1, is disclosed in detail in commonly assigned design patent Holen U.S. Pat. No. 273,807 which is incorporated herein by reference.

Figure 2:
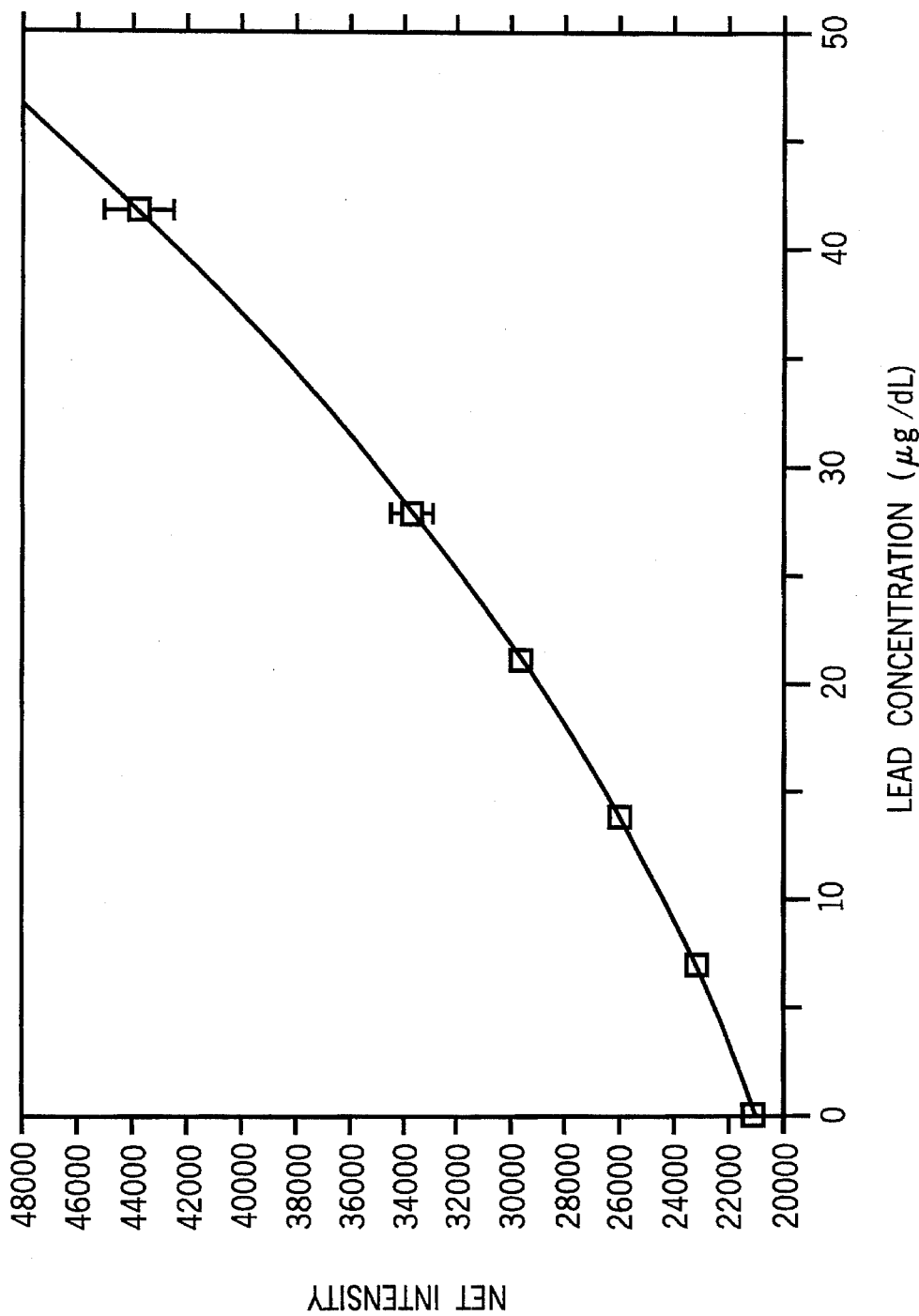
FIG. 2 is a standard curve for an IMx® Analyzer.

FIG. 2 is a standard curve plotting the fluorescence intensity obtained for each of the six aqueous lead standards described above in an assay conducted in accordance with the present invention. The automated IMx assay procedure used to generate fluorescence data on each of the lead standards is as follows:

300 µL of each aqueous lead standard is dispensed by hand into the sample cup of duplicate sample cartridges (see FIG. 1) of the IMx carousel. The steps enumerated below are performed automatically on each of the aqueous standards by a pre-programmed IMx instrument without operator intervention. The transfer of reagents from the reagent pack to the sample cartridge, and among the various compartments of the sample cartridge and the cuvette, is performed by the IMx robotic pipetting arm. Fluorescence intensity readings are taken on the assay solution in the IMx cuvette using the IMX FPIA optical assembly without polarization. The reagent pack, reagent wells, sample cartridge, sample cup, cuvette and pre-dilute well referred to in the steps below are references to commercially known elements of the IMx instrument and are depicted schematically in FIG. 1.

1. A blank read is performed on the empty IMx cuvette.
2. 100 µL of the aqueous lead standard sample is transferred out of the sample cup and into the pre-dilute well of the sample cartridge.
3. 100 µL of neutralizing buffer is transferred from reagent well 1 to the predilute well.
4. 100 µL phosphate dilution buffer (100 µL) is transferred from the buffer container of the IMx® instrument (not shown in FIG. 1) to the predilute well of the sample cartridge.
5. 150 µl of the neutralized aqueous lead standard present in the pre-dilution well is transferred into the cuvette.
6. 100 µL of the ALAD enzyme reagent is transferred from reagent well 2 into the cuvette.
7. 100 µL phosphate dilution buffer is transferred from the IMx buffer container into the cuvette.
8. The assay solution present in the cuvette (neutralized sample, ALAD enzyme reagent and phosphate dilution buffer) is permitted to incubate for 5.67 minutes.
9. 100 µL of substrate reagent is transferred from well 3 of the reagent pack into the cuvette follwed by 100 µL of phosphate dilution buffer.
10. The reaction mixture now present in the cuvette (ALAD enzyme reagent, substrate reagent, neutralized sample, and phosphate buffer) is permitted to incubate for 25 minutes.
11. 200 µL Ehrlich's reagent is transferred from well 4 of the reagent pack to the cuvette, followed by 25 µL of phosphate dilution buffer, followed immediately by 200 µL of Ehrlich's reagent and 500 µL of phosphate dilution buffer.
12. The reaction mixture in the cuvette (enzyme, substrate, sample, buffer and Ehrlich's reagent) is permitted to incubate for 5.67 minutes.

13. A reading is taken of fluorescence intensity of the assay solution in the cuvette using the optical equipment of the IMx® at 485 nm for excitation and 525 nm for emission.

Results

Table 5 below reports the measured net fluorescence intensity of each replicate of the aqueous standards. This data is used to obtain the standard curve depicted in FIG. 2.

TABLE 5

| Standard | IMx ® Net Intensity (units) | | | |
|---|---|---|---|---|
| lead (µg/dL) | rep a | rep b | Average | Stdev |
| 0 | 21031 | 20833 | 20932 | 140 |
| 7 | 22854 | 23205 | 23030 | 248 |
| 14 | 25592 | 25937 | 25765 | 244 |
| 21 | 29741 | 29425 | 29583 | 223 |
| 28 | 33943 | 33036 | 33490 | 641 |
| 40 | 44621 | 42825 | 43723 | 1270 |

EXAMPLE 6

Automated Whole Blood Lead Assay Using the IMx® Benchtop Analyzer

Materials

All reagents used are available commercially. The d-aminolevulinic acid dehydratase (ALAD), 4-dimethylaminobenzaldehyde (DMAB) and sodium azide are purchased from Sigma Company of St. Louis, Mo., as cat. nos. A-0644, D-8904 and S-2002 respectively. D-Aminolevulinic acid (ALA), 2,2 -bis (hydroxymethyl)-2,2'2"-nitrilotriethanol (Bis-Tris), citric acid, 8-hydroxyquinalone-5-sulfonic acid (HQSA), 10 mg/dL lead volumetric standard and concentrated nitric acid ($HNO_3$) are purchased from Aldrich Chemical Co., Milwaukee, Wis., as cat. nos. A5,990-5, 15,666-3, 25,127-5, H5,875-7, 31,902-3 and 22,571-1, respectively. Tris(2-carboxyethyl)-phosphine (TCEP) is purchased from Pierce, Rockford, Ill. as cat. no. 20490. Rhodamine 116 is purchased from Eastman Kodak, Rochester, N.Y. as cat. no. 1369040. Glacial acetic acid is purchased from Mallinckrodt, Paris, Ky. as cat. no. V194. Concentrated hydrochloric acid (HCl) is purchased from Baker, Phillipsburg, N.J. as cat. no. 9535-3. HPLC grade water is purchased from EM Science, Gibbstown, N.J., as cat. no. WX0004-1. 1004 µg/dL zinc chloride aqueous standard is purchased from SPEX, Edison, N.J., as cat. no. AQZN2-500. Trichloroacetic acid (TCA) is purchased from GFS Chemicals, Columbus, Ohio as cat. no. 390. Polyethylene glycol 8000 (PEG 8000) is commercially available from a variety of known sources. A phosphate dilution buffer was prepared containing 1M phophate and 0.1% sodium azide.

Whole blood is collected from 3 donors of blood type O+ and B+ into Li heparin vacutainers and pooled. The endogenous lead level of the pooled blood is measured via graphite furnace atomic absorption spectroscopy (Hitachi Z-8270) and is found to be 1.28 µg/dL lead. A portion of the 1.28 µg/dL lead blood pool is spiked to 40 µg/dL lead by gravimetric dilution of the 10 mg/dL lead stock, and the actual lead concentration is determined via graphite furnace atomic absorption spectroscopy and found to be 40.28 µg/dL. The atomic absorption spectroscopy was carried out in a known manner as follows.

Atomic Absorption Procedure

The instrumentation used is a Hitachi Z-8270 graphite furnace polarized Zeeman atomic absorption spectrophotometer and a Hitachi SSC-300 autosampler. The spectrophotometer is interfaced to a NEC Powermate 433 computer. Instrument settings for Pb+2 testing were optimized according to recommendations from the manufacturer. Absorbance was measured at a wavelength of 283.3 nm. 15 µM injection volume was dispensed by the autosampler onto pyrolyrically coated graphite platform cuvettes. Graphite furnace settings for Pb+2 testing are:

| | Temp., (°C.) | | Time, (sec) | | Gas Flow |
|---|---|---|---|---|---|
| Stage | Start | End | Ramp | Hold | (mL/min.) |
| Dry | 70 | 140 | 30 | 15 | 200 |
| Ash | 140 | 650 | 30 | 10 | 200 |
| Atomize | 2400 | 2400 | | 6 | |
| Clean | 2800 | 2800 | | 4 | 200 |
| Cool | | | | 5 | 200 |

The materials used in the atomic absorption analysis are as follows: Pb+2 standards are prepared by gravimetric dilution from a 10 mg/dL Pb+2 volumetric standard (Aldrich #31,902-3) into HPLC grade water (EM Science #WX0004). Human whole blood Pb+2 controls are purchased from BioRad (Lyphocheck #561,562 & 563). A Pb+2 matrix modifier is prepared consisting of 0.4% Ammonium Phosphate (Mallinckrodt #3484), 0.4% $HNO_3$ (Aldrich #22, 571-1) and 0.2% Triton X-100 (BioRad #161-0407) Standards, controls and specimens were tested in duplicate by measuring absorbance of the peak height. A standard curve was constructed of average peak height absorbance vs. Pb+2 concentration, and the Pb+2 concentrations for controls and specimens caluated off that curve.

A whole blood pretreatment reagent is prepared with 15% TCA and 1N HNO3. Neutralizing Buffer is prepared with 2.5M Bis-Tris, 30 mM HQSA, pH 7.60. ALAD Enzyme Reagent is prepared at pH 7.10 by diluting 5.8 U/mg ALAD 1/4 into a solution containing 250 mM Bis-Tris, 0.5% PEG 8000, 0.2% sodium azide and 5 µM rhodamine 116. Substrate reagent is prepared in HPLC water with 50 mM ALA, 25 mM TCEP, 40 µM zinc chloride, and 5 µM rhodamine 116. Ehrlich's Reagent is prepared with 0.67M DMAB in a 60:40 mixture of glacial acetic acid and conc. HCl. The neutralizing buffer, ALAD enzyme reagent, substrate reagent, and Ehrlich's reagent were placed into reagent wells of the IMx® reagent pack as represented in FIG. 1.

Aqueous lead standards at 0, 7, 14, 21, 28 and 42 µg/dL were prepared by gravimetric dilution from a 10 mg/dL stock lead solution into 75 mM citric acid at pH 0.90. The actual lead concentrations of the samples as determined by atomic absorption spectroscopy are 0.00, 6.66, 13.58, 21.88, 29.32 and 43.57 µg/dL, respectively.

Method

The concentration of lead in two whole blood samples is determined using a computer driven IMx® lead assay according to the present invention. The results are compared with the lead concentrations measured for the same two blood samples using atomic absorption. The two whole blood samples, found by atomic absorption to contain lead concentrations of 1.28 µg/dL and 40.28 µg/dL, respectively, were pretreated using a 70:30 ratio of blood to pretreatment peagent. The blood/acid mixture is vortexed vigorously, centrifuged 20 min. at 5,000 xg, and the supernatant removed and saved for testing.

Figure 5:
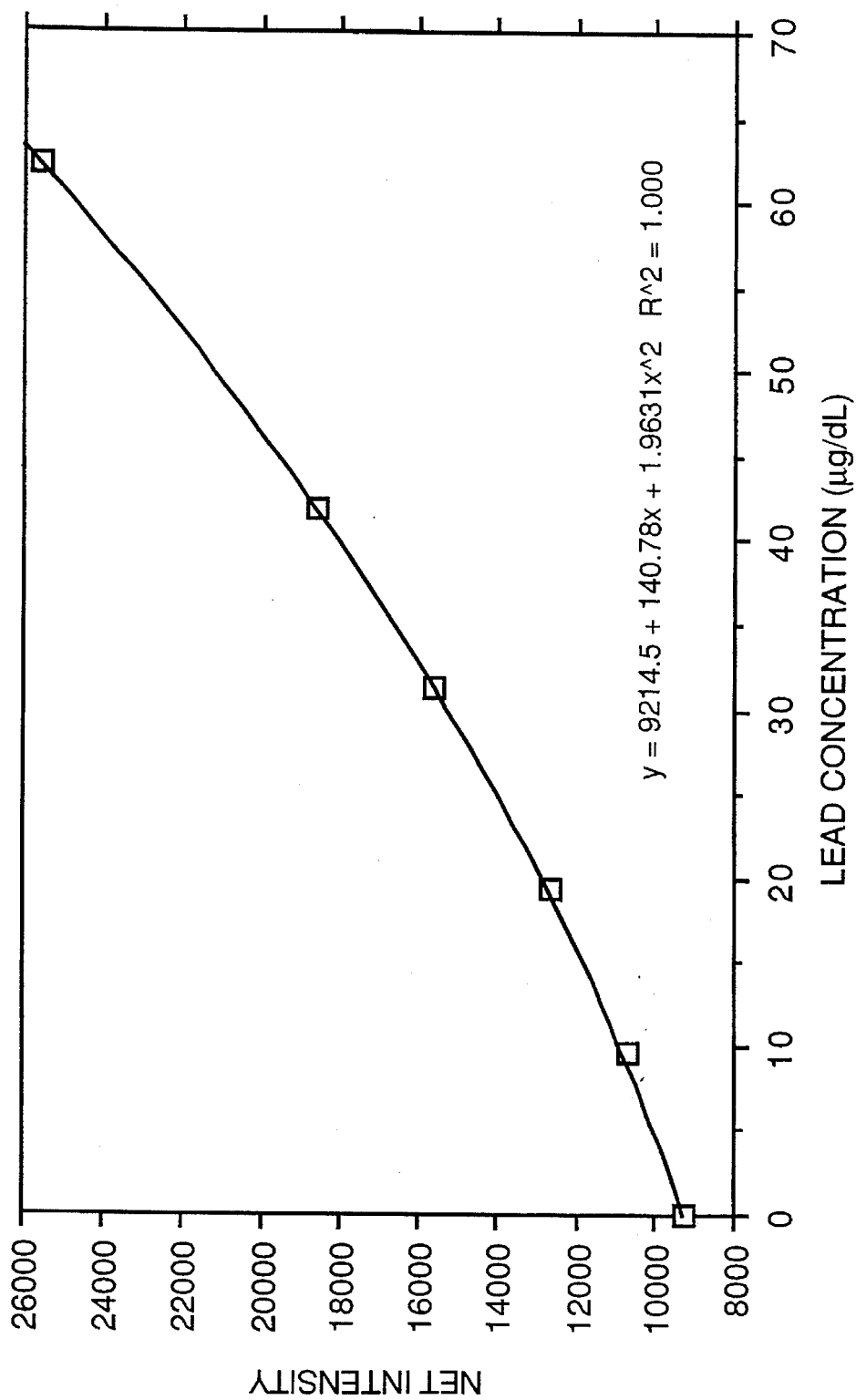
FIG. 5 is a standard curve for an IMx® Analyzer.

The aqueous lead standards used in this example to develop the standard curve in FIG. 5 are not diluted 70:30 as are the blood supernatant samples. To compensate for the dilution of the blood supernatants, a corrected standard curve is prepared in which the atomic absorption assigned values for the standards are multiplied by 1.4286 before plotting the standard curve of FIG. 5. The resulting adjusted values for the standards are 0.00, 9.51, 19.39, 31.26, 41.88 and 62.24 µg/dL.

An IMx® automation protocol according to the present invention was performed in duplicate on each of the aqueous standards and on each of the two blood supernatants as follows:

1. A blank read is performed on the empty IMx cuvette.
2. 150 µL of sample is transferred out of the sample cup and into the pre-dilute well of the sample cartridge.
3. 90 µL of neutralizing buffer is transferred from reagent well 1 to the predilute well.
4. 50 µL TDx® dilution buffer is transferred from the buffer container of the IMx instrument (not shown in FIG. 1) to the pre-dilute well of the sample cartridge.
5. 100 µl of the neutralized sample is transferred from the pre-dilution well into the cuvette.
6. 90 µL of the ALAD enzyme reagent is transferred from reagent well 2 into the cuvette.
7. 135 µL TDx® dilution buffer is transferred from the IMx buffer container into the cuvette.
8. The assay solution present in the cuvette (neutralized sample, ALAD enzyme reagent and TDx® dilution buffer) is permitted to incubate for 6.25 minutes.
9. 90 µL of substrate reagent is transferred from well 3 of the reagent pack into the cuvette followed by 100 µL of TDx® dilution buffer.
10. The assay solution now present in the cuvette (ALAD enzyme reagent, substrate reagent, neutralized sample, and TDx® buffer) is permitted to incubate for 27.5 minutes.
11. 210 µL Ehrlich's reagent is transferred from well 4 of the reagent pack to the cuvette, followed by 325 µL of TDx® dilution buffer.
12. The reaction mixture in the cuvette (enzyme, substrate, sample, buffer and Ehrlich's reagent) is permitted to incubate for 6.25 minutes.
13. A reading is taken of fluorescence intensity of the assay solution in the cuvette using the optical equipment of the IMx® at 485 nm for excitation and 525 nm for emission.

Results

The average fluorescence readings obtained on the aqueous lead standards are set forth below in Table 6.

TABLE 6

| Lead Concentration in Aqueous Standard (µg/dl) | IMx Net Intensity |
| --- | --- |
| 0.00 | 9253 |
| 9.51 | 10674 |
| 19.39 | 12655 |

TABLE 6-continued

| Lead Concentration in Aqueous Standard (µg/dl) | IMx Net Intensity |
| --- | --- |
| 31.26 | 15564 |
| 41.88 | 18579 |
| 62.24 | 25566 |

From this data a standard curve was generated. The standard curve (shown in FIG. 5) is fitted to a second order polynomial equation. Net fluorescence intensity for each whole blood supernatant sample is calculated from the equation. Table 7 below compares the lead concentrations (µg/dL) detected by the automated IMx® lead assay of the present invention vs. the lead concentrations measured on the same samples using atomic absorption.

TABLE 7

| Atomic Absorption | Lead Concentration (As Measured by IMx ®) | | | | |
| --- | --- | --- | --- | --- | --- |
| | rep a | rep b | Average | Stdev | % Recovery |
| 1.28 | 1.13 | 1.41 | 1.27 | 0.20 | 99.2% |
| 40.28 | 40.84 | 40.10 | 40.56 | 0.40 | 100.7% |

EXAMPLE 7

IMx® Lead Assay Precision

Precision of the computer driven IMx® Lead REA was determined on 3 IMx® instruments. Materials used are as described in Example 6 except for whole blood. For this example, a pool of whole blood was prepared from 20 donors with endogenous lead values between 2 and 24 µg/dL.

The whole blood lead pool was pretreated using a 70:30 ratio of blood to pretreatment reagent. The blood/acid mixture was vortexed vigorously, centrifuged 30 min. at 5,000 xg, and the supernatant removed and saved for testing.

As in Example 2, the aqueous lead standards used to generate a standard curve were not pretreated. Thus, they are not diluted to 70% of their original concentration like the whole blood pool. To compensate for this dilution, the atomic absorption assigned values for the standards are multiplied by 1.4286 before plotting the standard curve. The resulting values for the standards are 0.00, 9.51, 19.39, 31.26, 41.88 and 62.24 µg/dL.

Standards were tested on each of 3 IMx® instruments in triplicate, and pretreated blood supernatant was tested on each IMx® in reps of 20. The automation protocol is that given in Example 2.

Results

A standard curve for each IMx® is generated with the adjusted lead values for the standards vs. the average IMx flourescence net Intensity, and fitted to a second order polynomial. Net fluorescence intensity for each individual whole blood replicate is calculated from the standard curve equation for it's IMx®. Table 8 shows the precision for the IMx® automated whole blood lead assay of the present invention.

TABLE 8

| | Lead Concentration (μg/dL) | | |
|---|---|---|---|
| rep | IMx #6063 | IMx #8736 | IMx #13922 |
| 1 | 18.3 | 14.2 | 15.2 |
| 2 | 16.3 | 13.4 | 14.0 |
| 3 | 16.0 | 13.6 | 14.8 |
| 4 | 17.2 | 13.8 | 13.3 |
| 5 | 14.9 | 12.8 | 10.2 |
| 6 | 16.3 | 13.9 | 13.2 |
| 7 | 12.5 | 13.8 | 13.1 |
| 8 | 15.4 | 13.5 | 15.5 |
| 9 | 11.3 | 15.0 | 14.6 |
| 10 | 13.3 | 12.8 | 13.3 |
| 11 | 14.2 | 11.8 | 12.8 |
| 12 | 12.9 | 11.0 | 15.5 |
| 13 | 12.4 | 13.7 | 14.1 |
| 14 | 15.4 | 15.7 | 14.4 |
| 15 | 15.1 | 15.4 | 13.5 |
| 16 | 14.7 | 14.2 | 15.5 |
| 17 | 15.8 | 13.6 | 13.5 |
| 18 | 14.6 | 16.9 | 13.0 |
| 19 | 14.8 | 11.5 | 15.6 |
| 20 | 15.1 | 14.2 | 14.9 |
| Average | 14.8 | 13.7 | 14.0 |
| Stdev | ±1.7 | ±1.4 | ±1.3 |
| CV | 11.5% | 10.1% | 9.3% |

EXAMPLE 8

Vision® Lead Assay

An automated lead assay according to the present invention is performed on an Abbott Laboratories Vision® analyzer as follows:

Materials

The materials used in this example are commercially available as follows: From Sigma Chemical Company, St. Louis Mo. is obtained the following: 5-Aminolevulinic Acid (ALA), catalog No A-3785; d-aminolevulinic dehydratase (ALAD) catalog no. A-0644; Bis-Tris buffer, catalog B-9754; dimethylaminobenzaldehyde (DMAB) catalog no. D-8904; Dithiothreitol (DTT), catalog no.D-0632; glutathione, catalog no. G-4251; lead nitrate, catalog no. L-6258; mercuric chloride, catalog no. M-6529; and trichloracetic acid (TCA), catalog no. T-6399. From Aldrich Chemical Company are obtained Histidine H1, catalog no. H1,520-9; Iminodiacetic acid (IDA), catalog no. I-120-0; sucrose, catalog no. 24,761-8; and zinc chloride, catalog no. 22,999-7. From Fisher Scientific, Faire Lawn N.J., are obtained: Glacial aceitc acid, catalog no. A38s-212; HPLC grade deionized water, catalog no. W5-4; nitric acid, catalog no. A200s-212; perchloric acid, catalog no A228-11b.

Reagent Solutions

1. Aqueous lead standards: Aqueous lead standards at concentrations of 0, 7, 14 and 28 μg/dl were prepared by dilution from an 8 mg/dl stock solution of lead nitrate nitrate. The dilutions were carried out using HPLC deionized water adjusted to a pH of 2.0 with nitric acid.
2. Aqueous neutralizing buffer: An aqueous neutralizing buffer is prepared containing 1.5M Bis-Tris, 0.5M IDA, 0.125M histidine. The pH of the solution was adjusted to 7.05 with concentrated nitric acid.
3. Neutralized lead standards: Each of the aqueous lead standards was combined with neutralizing buffer in a 60/40 volume ratio, respectively, to obtain neutralized lead standards.
4. ALAD enzyme solution: A buffer solution is first prepared by dissolving 10.08 grams of Bis-Tris, 21.40 grams of sucrose in 250 ml water. DTT was added to the solution to obtain a concentration of 6.25 mM. The solution was then adjusted to pH 6.9 with nitric acid and allowed to incubate for about 90 minutes at room temperature. ALAD was diluted 1/5 (by weight) into this buffer. The ALAD solution is then adjusted to pH 7.1.
5. ALA substrate solution: An aqueous solution of ALA containing 0.25M Bis-Tris, 0.125M sucrose, 10 mM ALA, and 2.5 mM glutathione is prepared by combining 5.22 g Bis-Tris, 4.28 g sucrose, 0.17 g ALA, 0.077 g glutathione and xxg ZnCl2 to sufficient water to reach a final volume of 100 ml. The pH was adjusted to 6.9 with concentrated nitric acid.
6. Stop buffer. A solution was prepared containing 10% TCA and 0.1M mercuric chloride. A stop buffer is prepared by combining 5.01 grams of TCA and 1.36 grams mercuric chloride in sufficient water to bring the total weight of the solution to 53.28 grams.
7. Ehrlichs Reagent is prepared by mixing 10 g DMAB with 420 ml glacial acetic acid, and 80 ml perchloric acid.

Vision® Assay Procedure

Figure 3:
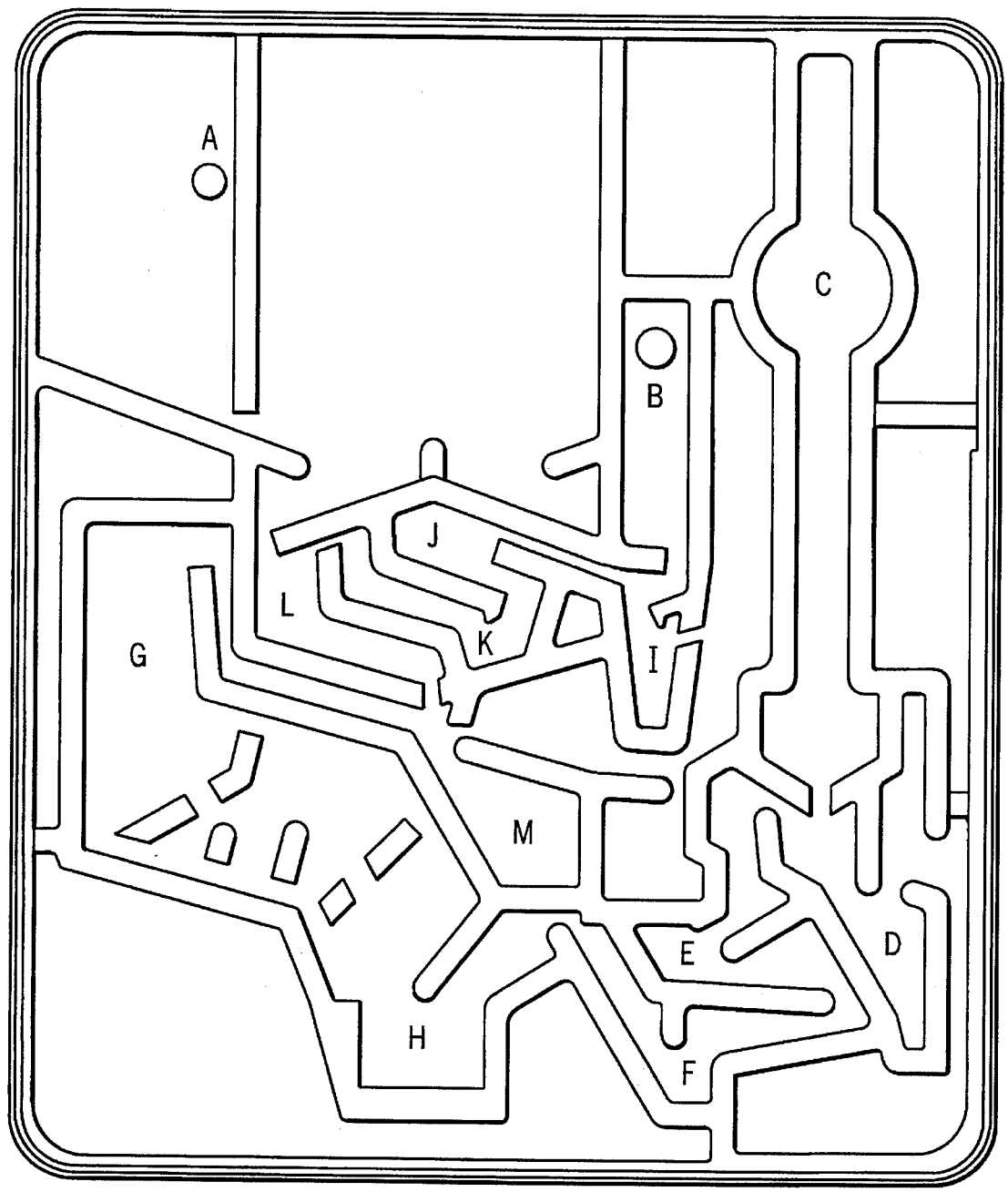
FIG. 3 is a schematic diagram of an Abbott Vision® Analyzer Test Cartridge.

Each of the 4 aqueous lead standard solutions prepared above are run on the Vision® analyzer using the test cartridge shown in FIG. 3. Referring to the test cartridge shown in FIG. 3, the following assay steps were carried out for each of the standard solutions:

(a) 50 μl of the neutralized standard solution are added to the sample well C of the test cartridge. The test cartridges are then loaded onto the centrifuge platter of the Vision® analyzer and the instrument is started with the test packs in the "install" position as shown in FIG. 3. While the Vision® centrifuge platter is spinning, the instrument rotates the test cartridge counterclockwise 90° to the "mix" position for 5 seconds and then clockwise 90° again back to the install position for 5 seconds. Two mix-install cycles are performed in order to transfer the sample from the sample well C to the reading chamber H of the test cartridge. The path of the sample is as follows:

$$\text{install: C} \longrightarrow \text{D}$$
$$\text{mix: D} \longrightarrow \text{E}$$
$$\text{install: E} \longrightarrow \text{F}$$
$$\text{mix: F} \longrightarrow \text{G}$$
$$\text{install: G} \longrightarrow \text{H}$$

(b) The instrument was stopped and reagents were manually added to the test pack as follows: (i) 50 μl of the ALAD enzyme solution, prepared above, is placed in the reagent well A of the test cartridge; (ii) 50 μl of the substrate solution is placed in the sample well C of the test cartridge; and (iii) 110 μl of the stop buffer is put in reagent well B of the test cartridge.

(c) The test cartridge is reloaded onto the centrifuge platter of the Vision® analyzer. The instrument is pre-programmed to perform a mix-install cycle having duration of 5 and 3 seconds respectively. This mix-install cycle mixes the enzyme solution in reagent well A with the sample that is already present in the reading chamber in step (a) according to the following path:

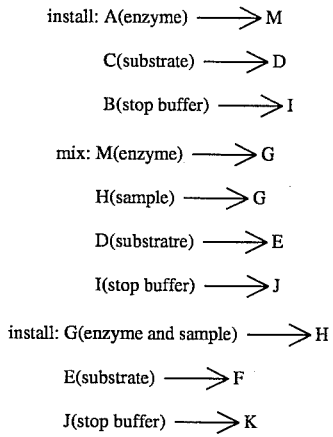

Thus, at the end of the mix-install cycle performed in this step (c), the enzyme solution has been mixed with the original sample and is now present in the reading chamber H along with the sample; the substrate solution has not yet combined with the enzyme sample mixture but is now positioned in region F; and the stop buffer has been moved to region K.

(d) The Vision® instrument is pre-programmed to retain the test cartridge in the install position for a period of 10 minutes to allow the sample solution and the enzyme solution to incubate in the reading well H.

(e) At the conclusion of the 10 minute incubation period of step (d) the Vision® analyzer is programmed to perform another mix-install cycle of 5 seconds (mix) and 1800 seconds (install). This mix-install cycle mixes the substrate with the sample/enzyme solution and permits a 30 minute incubation. The pathways for the substrate and the enzyme/sample mixture are as follows:

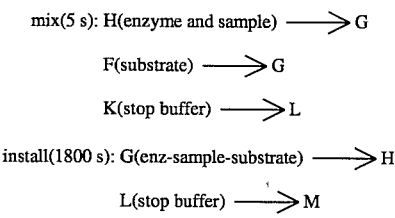

At the conclusion of this step (e) the assay solution present in the reading chamber has incubated 30 minutes and now contains the ALAD/ALA reaction product porphobilinogen.

(f) After the 30 minute incubation of the enzyme and substrate provided by the mix-install cycle of step (e), the Vision® performs a pre-programmed mix-install cycle to mix the stop buffer into the mixture of enzyme, substrate and sample. This mix-install cycle is mix (5 seconds) and install (5 seconds) and is performed three times. The mix-intall cycles transfer the stop buffer according to the following pathway:

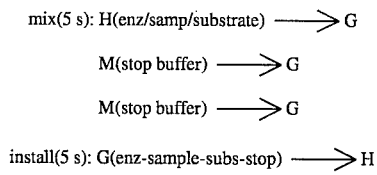

(g) The Vision® centrifuge stops, and 300 μl of Erlichs reagent (DMAB) is manually added to reagent well A. Several mix install cycles are performed to mix the Ehrlich's reagent with the assay solution. At the conclusion of this step, the colored assay solution is present in the reading chamber H of the test cartridge.

(h) Ten minutes after addition of the Ehrlich's reagent, the Vision® analyzer performs a colorimetric absorbance reading on the assay reaction mixture.

Results

Table 9 below shows the average absolute milliabsorbance for each duplicate set of the four aqueous lead standards. This data is used to plot the standard curve shown in FIG. 4.

TABLE 9

| Lead Concentration (μg/dL) | mAbsorbance |
| --- | --- |
| 0 | 2045 |
| 10 | 1668 |
| 20 | 1146 |
| 40 | 677 |

Figure 4:
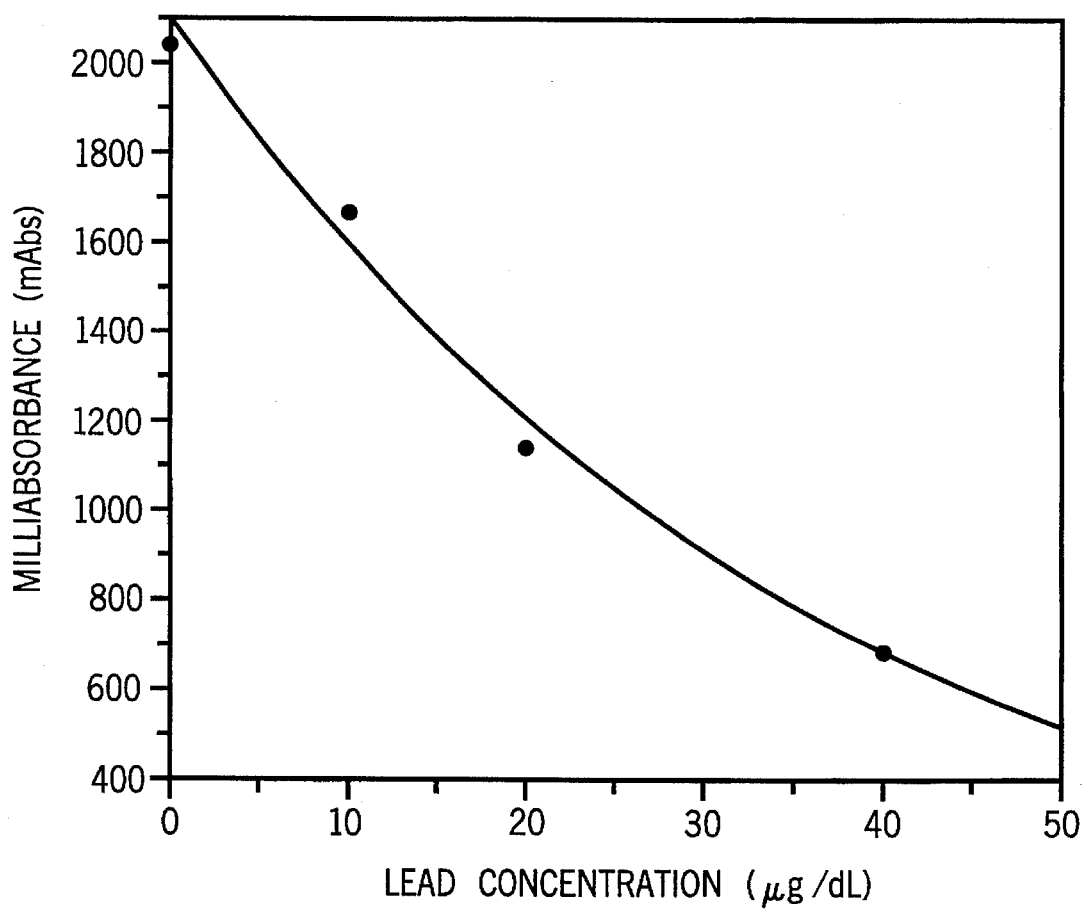
FIG. 4 is a standard curve for an Abbott Vision® Analyzer.

The standard curve shown in FIG. 4 is fitted to a second order polynomial equation. The standard curve is then used for subsequent assays of whole blood supernatants carried out in test cartridges on the Vision® analyzer as described above. The test cartridge of FIG. 3 can be modified so that it is pre-loaded with all of the reagents necessary to conduct the lead assay on the Vision® analyzer from start to finish without manual intervention other than loading the test cartridges onto the Vision® instrument, and removing them at the conclusion of the pre-programmed assay procedure. Commonly assigned U.S. Pat. No. 4,883,763 discloses the manner of supplying pre-loaded reagents in Vision® test cartridges such that the reagents are automatically dispensed when centrifugal force is applied to the test cartridges.

We claim:

1. An assay for detecting lead present in a sample of whole blood, comprising the steps of:
   (a) adding a lead recovery agent to a supernatant obtained from the blood sample, said supernatant comprising the lead;
   (b) adding to the supernatant a disulfide enzyme which is inhibited in the presence of lead; and
   (c) correlating the activity of the disulfide enzyme to the amount of lead in the blood sample.

2. The assay of claim 1 wherein the lead recovery agent has a lead binding constant in the range of about 6 log K to about 9 log K.

3. The assay of claim 1 wherein the supernatant is obtained from whole blood having a concentration of lead in the range of about 0.1 to about 20 μg/dl.

4. The assay of claim 1 wherein the supernatant of step (a) contains substantially all of the lead originally present in said whole blood sample in a form detectable in the assay, whereby the total amount of lead detected in the supernatant, as determined by step (c) of the assay, is at least 90% of the total amount of lead capable of being detected in said sample of whole blood by atomic absorption.

5. The assay of claim 1 wherein the lead recovery agent is at least one member selected from the group consisting of N-benzyliminodiacetic acid, ethylenebis(oxyethylenenitrilo) tetraacetic acid, ethylenediaminetetraacetic acid, L-histidine monohydrochloride monohydrate, N-(2-hydroxyethyl)iminodiacetic acid, iminodiacetic acid, DL-penicillamine, methyliminodiacetic acid, nitrilotriacetic acid, sodium citrate, and 8-hydroxyquinoline-5-sulfonic acid hydrate.

6. The assay of claim 1, further comprising the step of neutralizing the supernatant in the presence of the lead recovery agent.

7. The assay of claim 6 wherein the supernatant, following said neutralization step, contains at least 90% of the lead originally present in the blood sample and substantially all of said lead in the supernatant is detectable in said assay.

8. The assay of claim 1 wherein the lead recovery agent has a lead binding constant in the range of about 4 log K to about 13 log K.

9. The assay of claim 8 wherein the disulfide enzyme is an aminolevulinic acid dehydratase enzyme and the method further comprises the steps (i) adding aminolevulinic acid to the whole blood supernatant and (ii) incubating the enzyme and the aminolevulinic acid.

10. The assay of claim 9 wherein the steps of the assay are automated.

11. The assay of claim 10 wherein the activity of the enzyme is detected fluorometrically.

12. The assay of claim 11 wherein the assay is performed by an IMx® instrument.

13. The assay of claim 11 wherein the assay is performed by an AxSYM® instrument.

14. The assay of claim 10 wherein the activity of the enzyme is detected colorimetrically.

15. The assay of claim 14 wherein the assay is performed on a Vision® analyzer in a multi-chamber mixing cartridge rotatably mounted on a centrifuge platter.

16. An assay for detecting lead in a sample of whole blood, the assay comprising the steps of (i) adding an aminolevulinic acid dehydratase enzyme and aminolevulinic acid to an assay solution comprising a supernatant separated from the whole blood sample, wherein the supernatant, at the time of said addition, has a neutral pH and contains lead which was originally present in the whole blood sample; (ii) reacting said enzyme and aminolevulinic acid under conditions sufficient to produce porphobilinogen; (iii) detecting the amount of porphobilinogen produced in said reaction; and (iv) correlating the amount of porphobilinogen with the amount of lead in the sample; wherein the amount of lead detected in the supernatant as a result of steps (iii) and (iv) is at least 90% of the amount of lead which was present in the whole blood sample.

17. The assay of claim 16 wherein step (i) is carried out in the presence of a reducing agent selected from the group consisting of sulfhydryl compounds.

18. The assay of claim 16 performed without manual intervention by a pre-programmed analytical instrument.

19. The assay of claim 18 wherein, prior to step (i), the supernatant is combined with a lead recovery agent having a lead binding constant in the range of about 4 log K to about 13 log K.

20. The assay of claim 18 wherein step (i) is carried out in the presence of a tertiary phosphine.

21. The assay of claim 8 wherein step (iii) is carried out colorimetrically.

22. The assay of claim 8 wherein step (iii) is carried out fluorometrically.

23. A lead assay comprising the steps of:
a) forming an assay solution by combining a sample suspected of containing lead with (i) an enzyme which is inhibited in the presence of lead; (ii) a substrate capable of reacting with said enzyme to form a reaction product; and (iii) a fluorescer which does not react chemically with the enzyme, the substrate or the reaction product;

b) incubating the assay solution under conditions sufficient to produce said reaction product;

c) contacting the assay solution with a coloring reagent capable of converting said reaction product to a chromophore capable of changing the transmissive properties of the assay solution within a wavelength band that overlaps the excitation and/or emission wavelength band of the fluorescer;

d) irradiating the assay solution with light having a wavelength within the excitation wavelength band of the fluorescer;

(e) measuring the fluorescence emitted by the assay solution as a measure of the concentration of lead in the sample.

24. The assay of claim 23 wherein the enzyme is an aminolevulinic acid dehydratase; the substrate is aminolevulinic acid; and the reaction product is porphobilinogen.

25. The method of claim 24 wherein the sample is a supernatant obtained from whole blood and said assay solution further comprises a lead recovery agent and a tertiary phosphine.

26. The assay of claim 23 performed automatically without operator intervention on a pre-programmed fluoresence detection instrument equipped with reagent pipetting, dispensing and storage means.

27. The assay of claim 26 wherein the fluorescer is a rhodamine dye.

* * * * *

UNITED STATES PATENT AND TRADEMARK OFFICE
CERTIFICATE OF CORRECTION

PATENT NO. : 5,597,702
DATED : January 28, 1997
INVENTOR(S) : Wong, et. Al.

It is certified that error appears in the above-indentified patent and that said Letters Patent is hereby corrected as shown below:

Column 28, line 13, change "claim 8" to --claim 18--.

Column 28, line 15, change "claim 8" to --claim 18--.

Signed and Sealed this

Tenth Day of June, 1997

Attest:

BRUCE LEHMAN

*Attesting Officer*   *Commissioner of Patents and Trademarks*